US012664422B2

(12) United States Patent
Hayes

(10) Patent No.: US 12,664,422 B2
(45) Date of Patent: Jun. 23, 2026

(54) EXPLAINABLE ARTIFICIAL INTELLIGENCE FROM MODAL INTERVAL ANALYSIS SOLUTIONS

(71) Applicant: Modal Technology Corporation, Minneapolis, MN (US)

(72) Inventor: Nathan Hayes, Minneapolis, MN (US)

(73) Assignee: Modal Technology Corporation, Minneapolis, MN (US)

( * ) Notice: Subject to any disclaimer, the term of this patent is extended or adjusted under 35 U.S.C. 154(b) by 954 days.

(21) Appl. No.: 17/875,891

(22) Filed: Jul. 28, 2022

(65) Prior Publication Data

US 2023/0062631 A1     Mar. 2, 2023

Related U.S. Application Data

(63) Continuation-in-part of application No. 17/791,623, filed on Jul. 8, 2022.
(Continued)

(51) Int. Cl.
*G06N 3/08* (2023.01)
*G16H 50/70* (2018.01)

(52) U.S. Cl.
CPC ............... *G06N 3/08* (2013.01); *G16H 50/70* (2018.01)

(58) Field of Classification Search
CPC ........... G06N 3/08; G06N 3/09; G16H 50/70; G16H 10/40
See application file for complete search history.

(56) References Cited

U.S. PATENT DOCUMENTS

| | | | |
|---|---|---|---|
| 7,554,540 B2 | 6/2009 | Hayes | |
| 7,949,700 B2 | 5/2011 | Hayes | |
| (Continued) | | | |

FOREIGN PATENT DOCUMENTS

| | | |
|---|---|---|
| CA | 3167215 | 7/2021 |
| CA | 3169187 | 1/2023 |
| (Continued) | | |

OTHER PUBLICATIONS

D.-w. Gong, Na-na Qin and Xiao-yan Sun, "Evolutionary algorithms for multi-objective optimization problems with interval parameters," 2010 IEEE Fifth International Conference on Bio-Inspired Computing: T, Changsha, China, 2010, pp. 411-420, doi: 10.1109/BICTA.2010.5645160 (Year: 2010).*
(Continued)

*Primary Examiner* — Matthew Ell
*Assistant Examiner* — Jonathan J Kim
(74) *Attorney, Agent, or Firm* — Schwegman Lundberg & Woessner, P.A.

(57) ABSTRACT

A method for extracting an explanation from a solution of a global optimization problem derived via an interval analysis is provided. In the context of a global optimization problem characterized by a model, a set of model parameters, and an objective function delimiting relationships between and among the set of model parameters, each model parameter in the set of model parameters corresponding to a unique solution interval of a set of solution intervals, a ranked order of significance for a solution interval in the set of solution intervals as a function of first and second endpoints of the solution interval is derived. Thereafter, an explanation to the solution of the global optimization problem is provided, the explanation embodied in a list or an index that effectively sorts model parameters in the set of model parameters as a
(Continued)

function of the ranked order of significance derived for a model parameter's corresponding solution interval.

12 Claims, 24 Drawing Sheets

Related U.S. Application Data

(60) Provisional application No. 63/226,793, filed on Jul. 29, 2021.

(56) References Cited

U.S. PATENT DOCUMENTS

| | | | |
|---|---|---|---|
| 9,529,778 | B2 | 12/2016 | Hayes |
| 9,588,736 | B2 | 3/2017 | Hayes |
| 9,934,198 | B2 | 4/2018 | Hayes |
| 11,526,727 | B1 * | 12/2022 | Mitchell ............... G06F 16/906 |
| 2002/0026294 | A1 * | 2/2002 | Grace .................... G16B 25/10 |
| | | | 702/190 |
| 2017/0060958 | A1 | 3/2017 | Van Rest et al. |
| 2019/0278826 | A1 | 9/2019 | Hayes |
| 2023/0041860 | A1 | 2/2023 | Hayes |

FOREIGN PATENT DOCUMENTS

| | | | | |
|---|---|---|---|---|
| KR | 20120024074 | A * | 3/2012 | ............. G06F 17/15 |
| WO | 2021142440 | | 7/2021 | |

OTHER PUBLICATIONS

M. G. Arnold, J. Garcia and M. J. Schulte, "The interval logarithmic number system," Proceedings 2003 16th IEEE Symposium on Computer Arithmetic, Santiago de Compostela, Spain, 2003, pp. 253-261, doi: 10.1109/ARITH.2003.1207686. (Year: 2003).*

Jiang, M., Hu, W., Qiu, L., Shi, M., & Tan, K. C. (Mar. 2018, March). Solving dynamic multi-objective optimization problems via support vector machine. In 2018 Tenth International Conference on Advanced Computational Intelligence (ICACI) (pp. 819-824). IEEE. (Year: 2018).*

A. K. Qin, X. Li, H. Pan and S. Xia, "Investigation of self-adaptive differential evolution on the CEC-2013 real-parameter single-objective optimization testbed," 2013 IEEE Congress on Evolutionary Computation, Cancun, Mexico, 2013, pp. 1107-1114, doi: 10.1109/CEC.2013.6557690. (Year: 2013).*

F. Mach, "Reduction of Optimization Problem by Combination of Optimization Algorithm and Sensitivity Analysis, " in IEEE Transactions on Magnetics, vol. 52, No. 3, pp. 1-4, Mar. 2016, Art No. 7003104, doi: 10.1109/TMAG.2015.2500026. (Year: 2016).*

Elmachtoub, A. N., & Grigas, P. (2020). Smart "predict, then optimize". Management Science, 68(1), 9-26. (Year: 2020).*

Z. Hu, "Research on Application of BP Neural Network Based on Genetic Algorithm in Multi-objective Optimization," 2016 8th International Conference on Information Technology in Medicine and Education (ITME), Fuzhou, China, 2016, pp. 681-684, doi: 10.1109/ITME.2016.0159. (Year: 2016).*

"International Application Serial No. PCT US2021 012951, International Preliminary Report on Patentability mailed Jul. 21, 2022", 6 pgs.

"U.S. Appl. No. 17/791,623, Preliminary Amendment filed Jul. 8, 2022", 10 pgs.

International Search Report and Written Opinion from PCT/US21/12951; Apr. 1, 2021; Lee Young; 7 pages.

Choromanska, A., et al. The Loss Surfaces of Multilayer Networks. Jan. 21, 2015. arXiv:1412.0233v3.

Hayes, N. Introduction to Modal Intervals. 2009. http://grouper.ieee.org/groups/1788/Material/Hayes_Modal%20Intervals.pdf.

Hinton, G., Vinyals, 0. and J. Dean. Distilling the Knowledge in a Neural Network. 2015. arXiv:1503.02531vl.

Kaucher, E. Interval Analysis in the Extended Interval Space IIR Computing Suppl. 2, pp. 33-49 , 1980.

Smith, L. A disciplined approach to neural network hyper-parameters: Part 1-learning rate, batch size, moment um, and weight decay. Mar. 26, 2018.

Sunaga, T. Theory of interval algebra and its application to numerical analysis. Research Association of Applied Geometry (RAAG) Memoirs vol. 2, pp. 29-46 , 1958.

Warmus, M. Approximations and Inequalities in the Calculus of Approx-imations. Bull. Acad. Polan. Sci. Ser. Math. Phys. vol. 9.4, pp. 241-245, 1961.

Warmus, M. Calculus of Approximations. Bull. Acad. Polan. Sci. vol. 4, pp. 253-259, 1956.

Stavros Adam, Dimitrios Karras, George Magoulas, and Michael Varhatis. 2015. Reliable estimation of a neural network's domain of validity through interval analysis based inversion. Conference: International Joint Conference on Neural Networks (IJCNN), At Killarney, Ireland.

Stavros Adam, George Magoulas, Dimitrios Karras, and Michael Varhatis. 2016. Bounding the Search Space for Global Optimization of Neural Networks Learning Error: An Interval Analysis Approach. Journal of Machine Learning Research 17, pp. 1-40.

Tal Ben-Nun and Torsten Hoefler. 2018. Demystifying Parallel and Distributed Deep Learning: An In-Depth Concurrency Analysis. arXiv:1802.09941v2.

Jerry Eriksson and Per Lindstrom. 1995. A Parallel Interval Method Implementation for Global Optimization Using Dynamic Load Balancing. Reliable Computing 1(1), pp. 77-91.

Carlos Hernández-Espinosa, Mercedes Fernández-Redondo, and Mamen Ortiz-Gómez. 2003. A New Rule Extraction Algorithm based on Interval Arithmetic. European Symposium on Artificial Neural Networks. Bruges (Belgium), pp. 155-160.

Anthony Leclerc. 1993. Parallel Interval Global Optimization and Its Implementation in C++. Interval Computations, vol. 3.

Arnold Neumaier. 2004. Complete Search in Continuous Global Optimization and Constraint Satisfaction. In A. Iserles, editor, Acta Numerica, vol. 13, pp. 271-369. Cambridge University Press.

Andreas Prell. 2016. Embracing Explicit Communication in Work-Stealing Runtime Systems. Ph.D. Dissertation. University of Bayreuth.

H. Ratscheck and R. L. Voller. 1991. What can interval analysis do for global optimization? Journal of Global Optimization 1, pp. 111-130.

D. Ratz. 1994. Box-Splitting Strategies for the Interval Gauss-Seidel Step in a Global Optimization Method. Computing, vol. 53, pp. 337-353. Springer Verlag.

Abhinav Vishnu, Charles Siegel, and Jeff Daily. 2017. Distributed TensorFlow with MPI. arXiv:1603.02339v2.

Nathan Hayes. 2018. Reliable Supervised Machine Learning with ALiX. Modal Technology Corporation.

* cited by examiner

ALiX™ ACCELERATOR

EXPLAINABLE ARTIFICIAL INTELLIGENCE FROM MODAL INTERVAL ANALYSIS SOLUTIONS

This application is a continuation-in-part of U.S. patent application Ser. No. 17/791,623 filed Jul. 8, 2022 which is a national phase election of Patent Cooperation Treaty (PCT) application Ser. No. PCT/US2021/012951 filed Jan. 4, 2021 and entitled RELIABLE MACHINE LEARNING USING INTERVAL ARITHMETIC, an application filed under 35 U.S.C. § 120 and 37 CFR § 53(b) claiming priority, under 35 U.S.C. § 119(e) (1), of U.S. provisional application Ser. No. 62/958,959, filed on Jan. 9, 2020 and entitled PARALLEL NONLINEAR GLOBAL OPTIMIZATION USING INTERVAL ARITHMETIC, the instant application claims priority pursuant to 35 USC § 120 to U.S. provisional application Ser. No. 63/226,793, filed on Jul. 29, 2021 and entitled EXPLAINABLE ARTIFICIAL INTELLIGENCE FROM MODAL INTERVAL ANALYSIS SOLUTIONS, each and every cited application incorporated herein by reference in its entirety.

TECHNICAL FIELD

The present invention is generally directed to systems and/or methods for reliable supervised machine learning, more particularly, to systems, processes, and/or methods of/for extracting explanations from solutions of global optimization problems solved by machine learning systems, the systems, processes, and/or methods utilizing interval analysis and modal interval arithmetic to extract an explanation from a solution to a global optimization problem, the explanation provided as output in the form of a list or an index of model parameters for an artificial neural network (or, more generally, a model), wherein the output is sorted as a function of each model parameter's ranked order of significance in solving the global optimization problem.

BACKGROUND

Machine learning, part-and-parcel of artificial intelligence (AI), is a field of study wherein systems are devised to learn without being explicitly programmed. A well-known formalism on the topic by Professor Tom Mitchel is often cited: "A computer program is said to learn from experience E with respect to some class of tasks T and performance measure P, if its performance at tasks in T, as measured by P, improves with experience E." (Mitchel, *Machine Learning*, McGraw-Hill International Editions Computer Science Series, 1$^{st}$ Ed.).

Supervised machine learning is the process of training a machine to make predictions based upon patterns found in data, with "learning" predicated upon a model (i.e., an artificial neural network), data (i.e., labeled data), and the training (i.e., the "exercise" of prediction refinement—machine tuning). Wikipedia notes that "[s]upervised learning is the machine learning task of learning a function that maps an input to an output based on example input-output pairs. It infers a function from labeled training data consisting of a set of training examples. In supervised learning, each example is a pair consisting of an input object (typically a vector) and a desired output value (also called the supervisory signal). A supervised learning algorithm analyzes the training data and produces an inferred function, which can be used for mapping new examples." By this definition, the inferred function may also be known as the "solution" to the model.

Mathematically, the machine of the supervised machine learning process consists of a model. Artificial neural networks, among other things, have proven to be powerful models for machine learning. Three common types of artificial neural networks are Convolutional Neural Network (CNN), Long Short Term Memory (LSTM), and Multi-Layer Perceptron (MLP). They are popular because they have proven to be effective, namely CNN for image recognition, LSTM for predicting time-series data, and MLP for a wide range of general classification and regression tasks. MLP is also regarded as a "universal function approximator" since it can learn to approximate any function to within a certain error, thus making MLP an industry workhorse.

As notionally articulated by the U.S. Defense Advanced Research Projects Agency (DARPA), the four waves of AI refer to the state of artificial intelligence capabilities, namely, those characterized by reasoning, learning, explaining, and critical thinking. Currently, as an "industry," AI is in the second wave characterized by statistical machine learning. A common feature of these systems is that the AI learning process uses randomization and statistical methods to produce an outcome, and the AI learning process itself is often described as a "black box" with no means to "look" inside or to extract any meaningful explanation as to how the machine reaches a particular "solution." Each system feature, as will be subsequently taken up, is a deterrent to meaningful advance in the art so as to secure a differentiated desirable foothold in the third AI wave and beyond.

Prior Methodology

A broad class of machine learning, also known as supervised machine learning, is defined as a global optimization problem. If $f: \mathbb{R}^n \to \mathbb{R}$ is an n-dimensional objective function for a model and $\theta \subseteq \mathbb{R}^n$ is a domain of unknown model parameters, then the solution to the global optimization problem is defined as:

$$x^* = \underset{x \in \theta}{\mathrm{argmin}} \, f(x).$$

In other words, $x^* \in \theta$ is the global minimum, a point that minimizes the objective function, and the model obtains its optimal solution when model parameters are located at $x^*$.

In the context of supervised machine learning, the global optimization problem is essentially a data fitting problem, i.e., $\theta$ is a domain of unknown model parameters, the model is an artificial neural network, and $f$ is an objective function that is properly minimized to the global minimum when $x^* \in \theta$ is selected as the best fit for the training data.

In statistical machine learning systems, the objective function is minimized by a method called gradient descent. In this approach, the unknown model parameters are initialized to a random starting point $x_0 \in \theta$. After initialization, a sequence of steps are taken to calculate $$x_k = x_{k-1} - \alpha \cdot \nabla f(x_{k-1}),$$

where $\nabla f(x)$ is the gradient of $f$ at x, and $\alpha$ is a scaling factor known as the "learning rate." In theory, the sequence $x_1$, $x_2$, . . . converges to a critical point $x_p \in \theta$ as the gradient of $f(x_{k-1})$ approaches zero, i.e., the gradient of $f(x_p)$ is an n-dimensional vector of zeros.

The main shortcoming of gradient descent is that the critical point $x_p$ may be a local minimum of the objection function, but there is no guarantee it will be the global minimum. In other words, there is no guarantee that $x_p = x^*$ will ever be true.

Additionally, since $x_0$ is initialized with random values, gradient descent may converge to different local minimums, depending on the initial value of $x_0$. In practice, this means gradient descent will not converge to the same answer for two different runs, since each run will initialize $x_0$ with a different set of random values.

Thus, for some runs, gradient descent may minimize the objective function "better" than other runs, and a large number of runs may be required to find the "best" solution. However, even if the machine performs thousands or millions of runs, there is no guarantee that the "best" solution will actually be the "correct" solution located at the global minimum. These deficiencies of gradient descent are responsible for the statistical and probabilistic nature of current machine learning systems that comprise the second wave of AI, and they form a first significant motivation behind the third wave of AI.

Advances promised through supervised machine learning can only be realized if there is high confidence in the results produced. Reduction in human and computer time and costs will provide faster research turnarounds through a more efficient use of data science, informatics, and information technology. In furtherance thereof, and notionally, the application of interval arithmetic to nonlinear globalization is known, having been set forth by Ratcscheck & Voller (see e.g., *What can interval analysis do for global optimization?* Journal of Global Optimization 1, pp. 111-130, June 1991).

Instead of initializing model parameters with random numbers, each model parameter is initialized as an interval having a lower and upper bound, the initialized elements of the model parameters forming an axis-aligned parallelotope (i.e., a "box") that defines a search region for the entire model parameter space. While such initialization guarantees a convergence to a global minimum (i.e., "the" global minimum), a powerful advantage relative to gradient descent approaches to supervised machine learning, data storage and/or processing remains an Achilles heel—the weak link if you will.

Heretofore known interval based supervised machine learning teachings have yet to address the sheer magnitude and complexity of the resulting nonlinear global optimization problems. The functions to be minimized, for example, routinely consist of, on the low end, $10^4$ variables, with $10^9$ variables not unheard of. By comparison, known teachings contemplate the minimization of functions of only a few variables (see e.g., Ratz, *Box Splitting Strategies for the Interval Gauss-Seidel Step in a Global Optimization Method.* Computing, Vol. 53, pp. 337-353, Springer Verlag, 1994, or, Eriksson & Lindstrom, *A Parallel Interval Method Implementation for Global Optimization Using Dynamic Load Balancing.* Reliable Computing 1(1), pp. 77-91, 1995).

Moreover, the branch-and-bound procedure that characterizes an interval arithmetic approach to nonlinear global optimization requires maintaining a queue of unprocessed interval boxes, which is often sorted based on certain criteria, e.g., unprocessed interval boxes associated with the lowest bounds on the minimization function may be kept at the top of the queue (see e.g., Hansen & Walster, *Global Optimization Using Interval Analysis.* $2^{nd}$ ed., revised and expanded, CRC Press, 2003, or, Leclerc, *Parallel Interval Global Optimization and Its Implementation in C++.* Interval Computations, Volume 3, 1993). If the number of variables to be minimized is fairly small, practical implementations can store the unprocessed interval boxes in containers provided by the standard libraries of popular programming languages such as C++ or Java. As the number of variables increases by orders of magnitude, such straightforward approaches quickly lead to memory exhaustion, even on modern computers with gigabytes of memory owing to the memory demands growing at a geometric rate with processing times become dominated by the container subroutines that manage the queue, inducing poor cache performance and fatal system crashes.

Thus, in light of the forgoing, it remains desirable and advantageous to greatly reduce the time and cost of training a machine while achieving both reproducibility and accuracy. Moreover, and more particularly, work remains outstanding in connection to global optimization problem solving, more particularly, in connection to systems and/or methods for model parameter determination of an objective function via a branch-and-bound interval arithmetic methodology for iterative bisecting a search region of model parameter space characterized by reduced system memory demands and/or improved data processing parallelism in furtherance of finding a global minimum of the objective function in connection to machine learning.

The Difficulty of Explainable AI

Turning now to the "black-box" nature of heretofore second wave AI solutions/solvers, third wave AI system designers remain steadfast in their utilization of statistical machine learning systems as the means by which to garner an explanation for the outcome. For example, suppose $\tilde{x} \in \theta$ is a solution obtained by training an artificial neural network to an acceptable level of accuracy from many runs of gradient descent. How does one go about determining which elements of $\tilde{x}$ are the most significant?

Contextually, and by non-limiting example, a life science research scientist may analyze blood protein data in order to identify patients who respond to different types of therapy or treatment. In this case, an artificial neural network will stratify patients, based on their blood proteins, into different therapy or treatment groups, allowing medical staff to provide a different therapy or treatment that is customized for each patient as a result of the patient's individual blood protein analysis.

Be that as it may, an even more important question the research scientist may like to have answered is "which proteins are the most significant factor in the stratification?" Armed with this knowledge, for example, the research scientist may be able to discover biological pathways for the disease that may lead to improved treatments, drugs, therapies, or cures, which would increase the quality of care for the patient.

An answer to this question is not provided by gradient descent, unfortunately, and this is why the artificial neural network, or the statistical machine learning system in general, is commonly referred to as a "black box." In other words, third wave AI systems seek to open up the "black box" and provide an explanation for the stratification produced by the artificial neural network, as, for example, in answering the question asked by the research scientist about which blood proteins are most significant to the patient stratification.

Currently, and illustratively, select elements of $\tilde{x}$ may be slightly perturbed by displacing them with a "tiny" offset. The accuracy of the artificial neural network can be measured for this perturbed solution and then compared to the accuracy of the solution at $\tilde{x}$. The sensitivity of the artificial neural network to changes in the perturbed elements will be deduced by comparing the difference in accuracy. Naturally, a higher difference implies that the perturbed elements are more significant than if the difference is small.

Such methods of trying to identify the significant elements of training solution $\tilde{x}$ may be fairly characterized as probabilistic and statistical, since it requires making small, arbitrary changes to an existing training solution x̃ and then measuring how the changes affect the outcome. While it may in some cases prove to be useful or effective, it suffers from practical and theoretical problems.

From a practical perspective, as the n-dimensional space of x̃ grows (due to a larger number of elements in x̃ required, for example, by a sophisticated model or artificial neural network), the computational requirements grow exponentially, to the point where useful explanations simply cannot be found with a practical amount of computation.

From a theoretical perspective, it is based on the solution x̃, which is obtained from another probabilistic and statistical technique (i.e., gradient descent). Hence, there is no guarantee that any of the explanations gleaned will be grounded in truth, since the entire process is analyzing the behavior of the model at x̃, which is most likely a false solution point, or local minimum. In other words, it is not analyzing behavior of the model at the global minimum x*, which is the only point where the model is guaranteed to have an optimal configuration.

Thus, in light of the foregoing, it remains desirable and advantageous to secure an outcome explanation for heretofore known machine learning applications. Moreover, and more particularly, work remains outstanding in connection to ascertaining which training solution elements most significantly contribute to a deterministic, reliable, and repeatable solution to a global optimization problem.

SUMMARY OF THE INVENTION

An interval arithmetic based system and method for solving a global optimization problem, in furtherance of, for example, supervised machine learning, is contemplated and provided. More particularly, a system/method characterized by a bisection indexing scheme for a parameter domain of an objective function and an attendant work stealing scheme is advantageously provided and disclosed.

Moreover, systems, processes, and methods are disclosed that require the use of interval analysis and interval arithmetic to extract an explanation from a solution to a global optimization problem, and the explanation is provided as output in the form of a list or index of model parameters for an artificial neural network (or, more generally, a model), wherein the output is sorted as a function of each model parameter's ranked order of significance in solving the global optimization problem.

The computer system is characterized by a central processing unit and a modal interval processing unit operably linked thereto, the modal processing unit characterized by a plurality of modal interval processing units, and memory accessible by the central processing unit. Memory components of the memory advantageously include a bisection context, a bisection queue, session data and training data. The bisection queue comprises a collection of bisection records characterized by integer fields (e.g., Axis, Item), Axis being an index to a particular array in the bisection context and Item being a record associated with the particular array element. The bisection context includes a plurality of arrays (e.g., Domain, Bottom, Top, and Subdomain), Domain and Subdomain being interval arrays, Bottom and Top being integer arrays, the arrays having a number of elements equal to a number of variables of an objective function to be minimized.

A preferred, robust, non-limiting method, contemplates receiving and storing a representation of the objective function in memory of the computer system. Each model parameter of model parameters of the objective function are initialized as an interval having a lower and upper bound such that initialized elements of the model parameters form an axis aligned parallelotope that delimits a search region S for an entirety of model parameter space. Domain is initialized such that every variable of the objective function has a corresponding interval domain value in Domain, the bisection queue being empty. Search region S in the Domain is divided/subdivided into subdomains. Thereafter, in connection to search region S dividing, a parallelization process is executed, the process characterized by workers in a work stealing scheme.

Each worker performs a depth-first search on a unique subset of the search region S while a breadth-first search is performed by workers in the work stealing scheme. For each worker, integers in Bottom represent a bisection status for Domain, the bisection status using an indexing scheme to record an interval subset restriction in each domain value in Domain. Each integer item in Top represents a subset of its corresponding item in Bottom, intervals in Subdomain representing a subset of the search region S in Domain. A bisection state is maintained via interaction between the bisection context the bisection queue, operations of the interactions characterized by Reset, Push, Pop, Remove and Cleanup operations.

As a nonlinear optimization solver, the contemplated system is relevant to the field of artificial intelligence, machine learning, and deep learning. In particular, the contemplated system abandons current industry trends and paradigms, providing an entirely different approach to training machines.

Existing systems and methods are based on a process known as gradient descent, which uses floating-point arithmetic. The well-understood and documented pain points of gradient descent can be reduced to its random "trial by error" nature as well as its inherently sequential computing process which makes it difficult to parallelize. The contemplated system abandons gradient descent in favor of a reliable process of "proof by elimination" based on interval arithmetic. Unlike gradient descent, the instant process is massively parallel and easy to scale. As a result, the contemplated system overcomes all of the known pain points of gradient descent, making it a significant improvement over the prior art.

As to explainable AI, Applicant's ranked order of significance relating to an index of model parameters in the form of an output, is obtained via a system or process that receives a solution to the global optimization problem in a format where each element of the solution is represented by a solution interval comprised of left and right endpoints, and each model parameter corresponds to a unique solution interval in the solution. For each solution interval, the distance between its left and right endpoints is determined as its ranked order of significance relative to all other solution intervals.

After the ranked order of significance is computed for every solution interval, all of the model parameters may be sorted, wherein each model parameter is sorted as a function of the ranked order of significance obtained for its corresponding solution interval, thereby producing an output that effectively orders every model parameter according to its significance in solving the global optimization problem.

After the output is obtained from the aforementioned system or process, the sorted model parameters can be used as an explanation that is provided as input to other various important systems, processes, or methods, all of which are predicated on the explanation provided by the sorted model parameters. Examples of such systems, processes, or methods include, but are not limited to, the discovery of significant model parameters, normalization of model data via insignificant model parameters, validation or falsification of scientific hypotheses, and model adjustment and/or refinement.

More specific features and advantages obtained in view of the summarized features will become apparent with reference to the drawing figures and DETAILED DESCRIPTION OF THE INVENTION.

BRIEF DESCRIPTION OF THE DRAWINGS

All figures have been prepared, and are included to facilitate and/or enhance an understanding of the basic teachings of the contemplated embodiments, and/or the concepts underlying same, and are incorporated in and constitute a part of this specification. While the drawings illustrate embodiments and context with respect thereto, and together with the description serve to explain principles of embodiments, other embodiments and many of the intended advantages of the disclosed systems, subsystems, devices, mechanisms, methods, operations, etc. will be readily appreciated as they become better understood by reference to the following detailed description and figures.

FIGS. 1-14 are provided herewith wherein:

FIG. 1 schematically depicts a preferred, non-limiting integrated system for training artificial intelligence applications;

FIG. 3 depicts a branch-and-bound process associated with the instant training for finding a global minimum of an objective function wherein each model parameter is initialized as an interval having lower and upper bounds, initialized elements forming an axis-aligned parallelotope that defines a search region, the search region interatively bisected;

FIG. 4 schematically depicts process virtual address space for the contemplated process methodology;

FIG. 5 graphically represents an advantageous, non-limiting bisection indexing scheme part-and-parcel of the instant training system/method;

FIGS. 7A-9D each schematically depicts a relatedness of/for process virtual address space memory components (FIG. 4), the parameter domain, and the indexing scheme (FIG. 5) in connection with a Pop operation, namely conditions/relationships before (FIG. 7A, 8A, 9A), during (FIG. 8B, 9B, 9C), and after (FIGS. 7B, 8B, 9C and 9D), as the case may be, as to the depicted operation;

FIG. 12 depicts a static structure diagram of an attendant, non-limiting worker and manager processes for contemplated system operations;

FIG. 13 depicts a sequence diagram of events of the worker and manager processes of FIG. 12; and, FIG. 14 schematically illustrates an explainable AI methodology in the context of the FIG. 3 branch-and-bound training process.

DETAILED DESCRIPTION OF THE INVENTION

Figure 1:
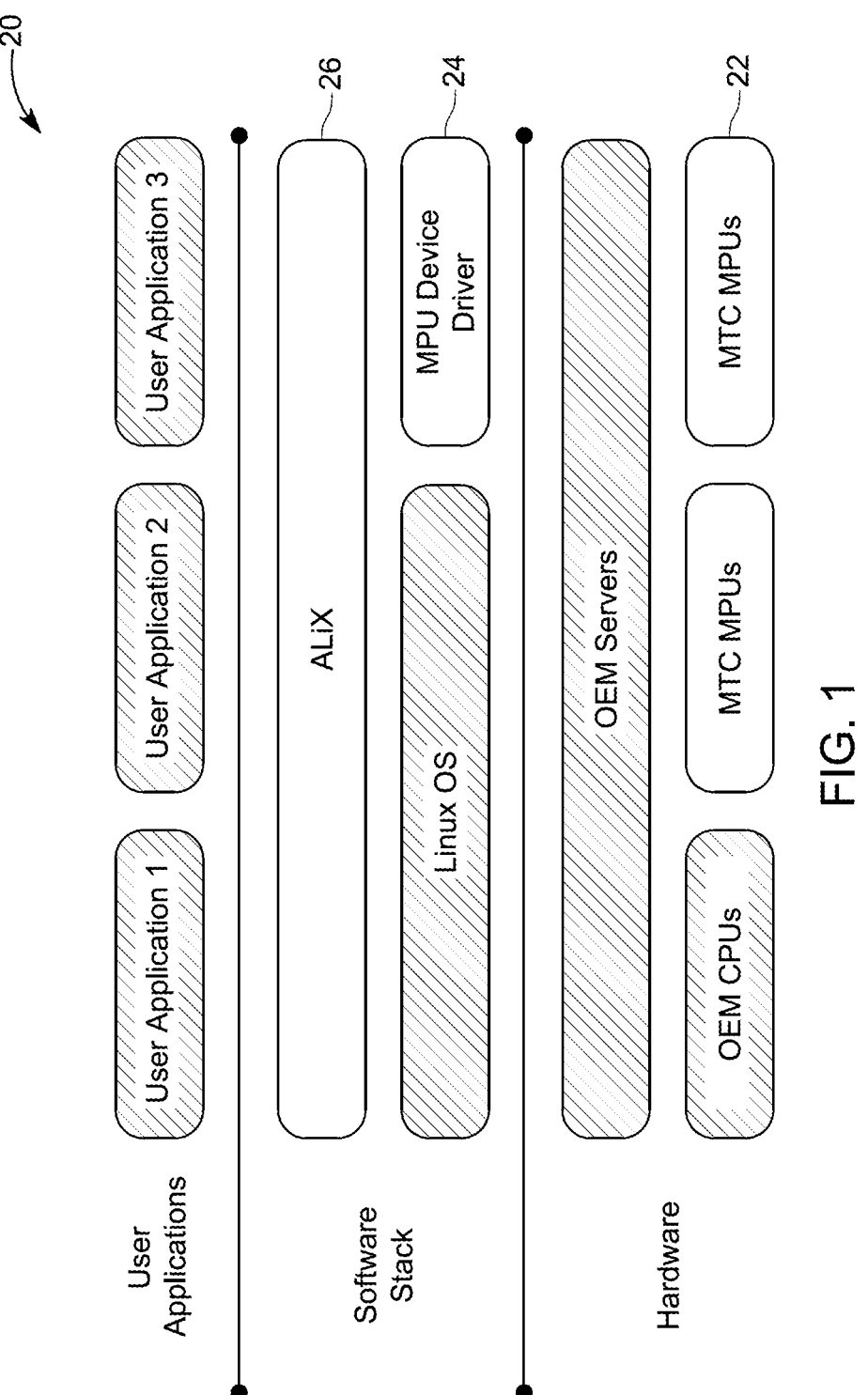

In advance of particulars for contemplated and advantageous systems and methods characterized by a novel application of interval arithmetic to tackle nonlinear global optimization problems, for example, and without limitation, artificial intelligence (AI), explainable AI, machine learning, and deep learning to name but a few, several preliminary observations are warranted.

First, Applicant has developed an innovative supervised machine learning system that replaces conventional and heretofore known systems and methods, based upon gradient descent backpropagation, with a novel approach based upon modal interval arithmetic. From its IEEE 1788 Working Group Paper captioned *Introduction to Modal Intervals* (August 2009), to its innovations in relation to improved utility in and for computational systems and methods as evidenced by U.S. Pat. Nos. 7,554,540, 9,529,778, 9,588, 736, and 9,934,198, each of which is incorporated herein by reference in their entireties, Applicant has leveraged its earlier work in addressing the shortcomings of known nonlinear global optimization approaches. Via the ability of the contemplated system/method(s) to employ multiple processors, multiple computers, or a combination of both, significant operational speed-ups are attainable.

Second, the contemplated and hereinafter described system and/or method perform the same linear algebra operations as current supervised learning methods, the difference being that elements of the matrices and vectors are modal intervals, not floating point values. While modern graphics processing units (GPUs) do not support modal interval arithmetic, current Applicant implementations of the system/methods emulate modal interval arithmetic operations in software on a central processing unit (CPU). In keeping with, among others, the teaching of the '736 & '198 patents, work continues on a modal interval arithmetic hardware accelerator, namely, a modal processing unit (MPU). In addition to computational speeds in keeping with floating point calculations, the MPU will provide data parallelism in the linear algebra operations for improved performance.

Third, heretofore unseen task parallelism is achieved for an interval arithmetic approach to model training by reimagining system memory utilization in combination with a novel bisection indexing scheme whose codes populates separate memory elements of the system and is thus overarching and correlative relative to same, greatly reducing memory requirements. Moreover, a hybrid parallelization is particularly well suited to support the domain bisections and operations attendant to the contemplated machine learning.

Fourth, methodologies to derive an explanation from a solution to a global optimization problem, in the context of minimizing the objective function $f$ via interval arithmetic, are disclosed. More particularly, an interval solution X* of the global optimization problem is provided as input, in a suitable format, where each element of X* is delimited as a solution interval [a,b] comprised of left (e.g., first) and right (e.g., second) endpoints a and b, respectively, and each model parameter of the artificial neural network (or, more generally, the model) corresponds to a unique solution interval in X.

Figure 2A:
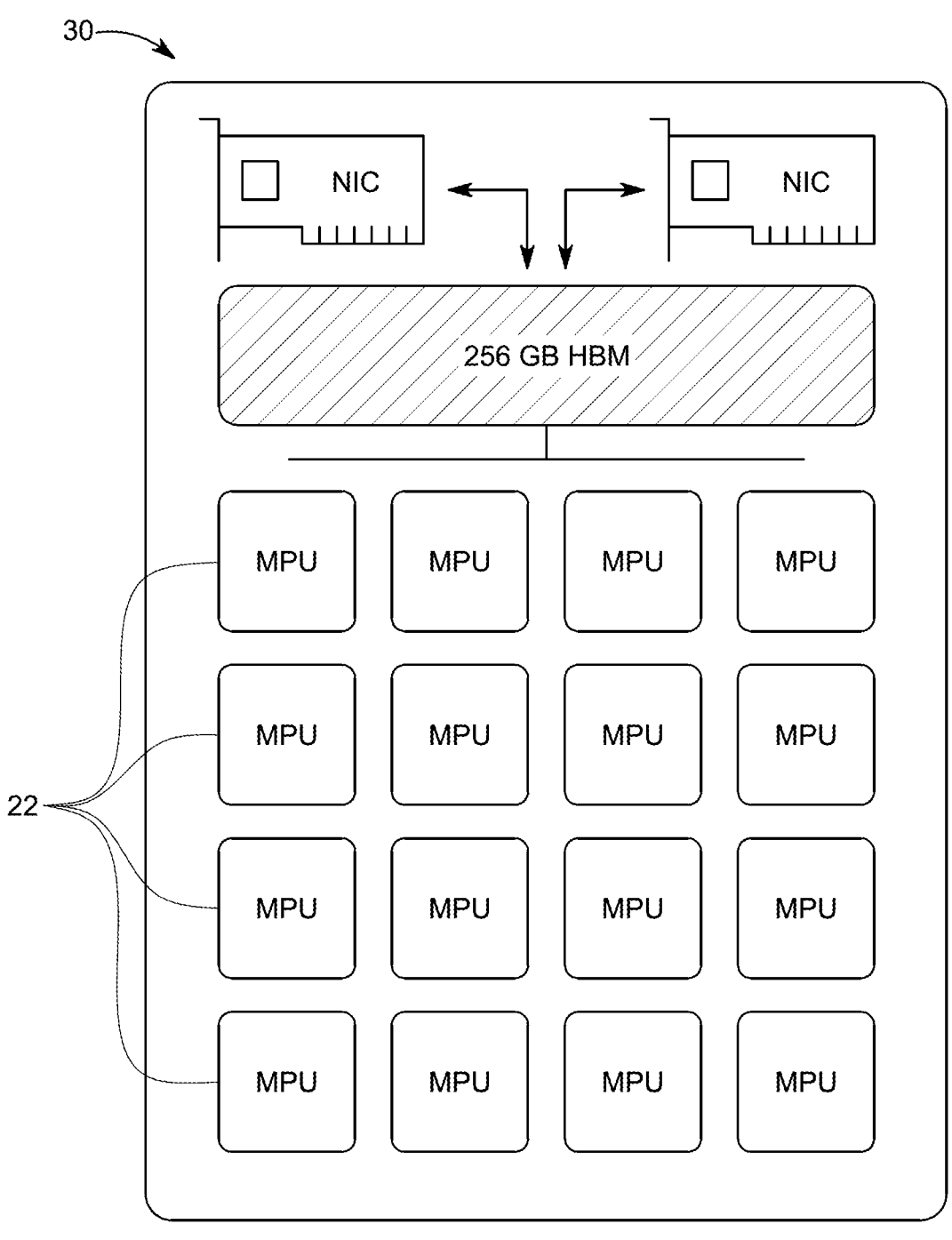
FIGS. 2A & 2B schematically depict contemplated, non-limiting elements of/for the integrated system of FIG. 1, namely, an accelerator on one hand, FIG. 2A, and a cluster comprised of central processing unit (CPU) servers and FIG. 2A accelerators on the other hand, FIG. 2B.
Figure 2B:
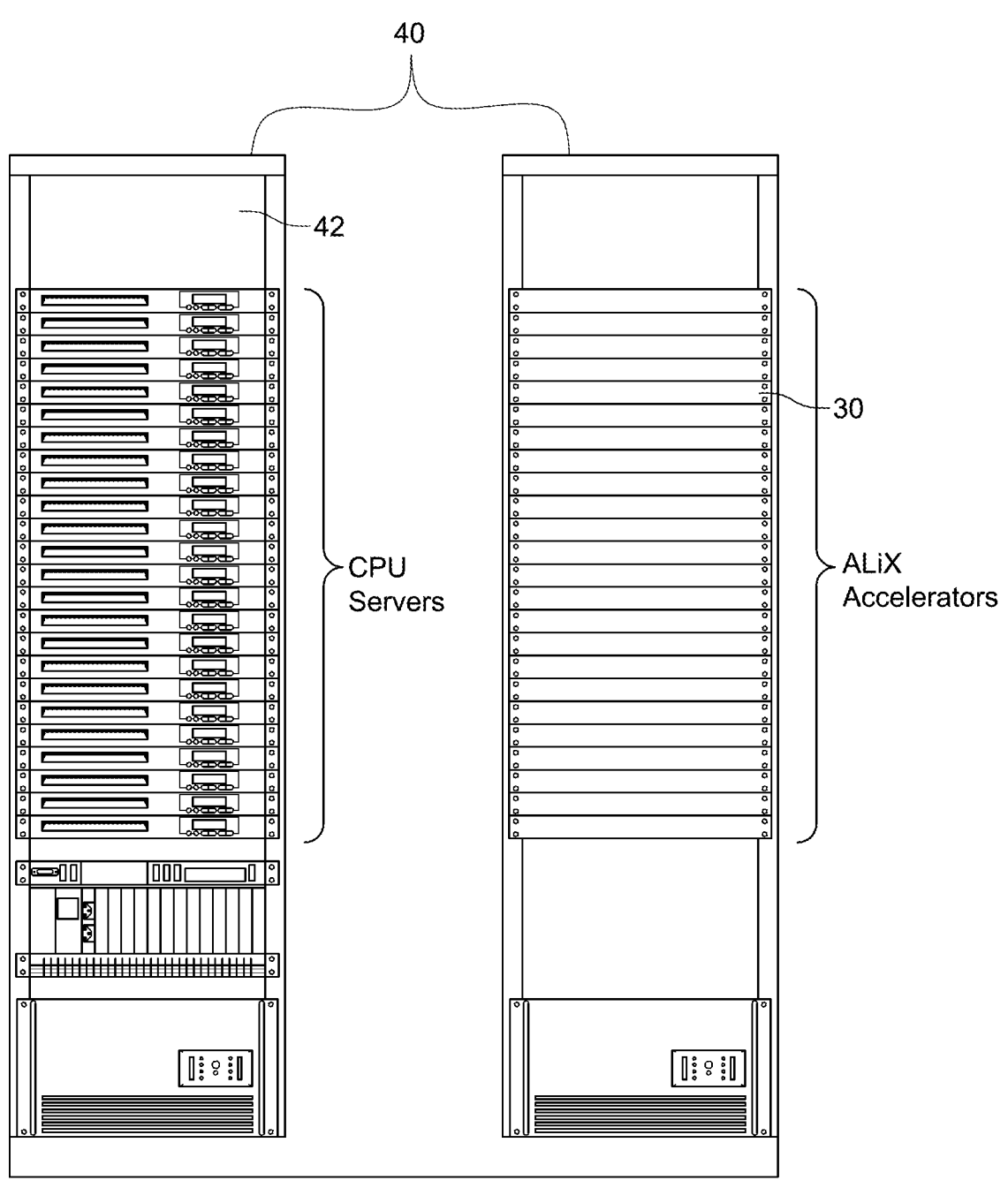

Finally, the following description commences with a presentation of a preferred non-limiting system/system particulars with reference to FIGS. 1, 2A & 2B. Thereafter, a preferred non-limiting machine training methodology is taken up with reference to FIGS. 3-11B, with particulars for worker and manager processes for contemplated system operations set forth in connection to FIGS. 12 & 13. The disclosure concludes with an overview and particulars for an advantageous, non-limiting explainable AI methodology, namely that depicted FIG. 14.

With general reference to FIGS. 1, 2A & 2B, schematic depictions of advantageous, non-limiting integrated systems/system elements for training artificial intelligence applications are set forth. System 20, FIG. 1, is notionally comprised of stacked hardware and software components or elements, namely, modal interval hardware (e.g., modal processing units (MPUs) 22 as indicated), a MPU driver 24, as circumstances may warrant, and software 26, with users advantageously, but not necessarily, able to develop supervised machine learning with such system. MPUs are hardware accelerators for performing interval arithmetic (see Applicant's earlier cited '736 patent). The MPU hardware accelerator provides GPU-like performance for modal interval arithmetic. MPUs can be installed side-by-side with GPUs for backward compatibility.

Notionally, modal interval hardware, e.g., chips advantageously manufactured by original equipment manufacturers (OEMs), will be used and leveraged by cloud service providers (CSPs), the CSPs installing/integrating the subject machine training system into their cloud infrastructure to provide interval machine learning to their end users. Alternately, a fully integrated hardware and software technology stack may be provided, more particularly, a technology stack that operates in the cloud infrastructure of the CSPs. End users access the technology stack via the cloud to train their artificial intelligence applications.

With reference to FIG. 2A, a training accelerator 36, embodied, for example and without limitation, in a standard 1U rack mountable form factor is contemplated, the accelerator characterized by modal interval hardware, namely, one or more MPUs 22. A training cluster 30, FIG. 2B, is likewise contemplated, without limitation, the cluster characterized by central processing unit servers 32 and the plural training accelerators 36.

Training accelerator components generally include one or more network interfaces, memory, and one or more MPUs. In a preferred embodiment, the MPUs are hardware circuits capable of performing large amounts modal interval arithmetic operations very quickly, preferably in a single instruction, multiple data (SIMD) format and performance factor. The MPUs are connected to memory. In the preferred embodiment, all of the MPUs share a common virtual address space which is comprised of physical high bandwidth memory (HBM). Also connected to the memory is one or more network interfaces that provide high speed, low latency access to the memory via an external network.

Also contemplated are variations within the system where essential components may take on different form factors or be replaced by different technology that serves the same functional purpose. For example, and without limitation, the rack mountable form factor of the training accelerator may be suitably replaced or substituted for/by/with a discrete card that connects directly to a motherboard of a CPU server via standard or proprietary bus protocols such as PCI Express, CCIX, or OpenCAPI. Moreover, and without limitation, a system that replaces the aforementioned discrete training accelerator card may be suitably replaced with an MPU directly integrated on the CPU itself, so that the combined function of the integrated CPU/MPU completely replaces the need for a discreet training accelerator at all. In every such system variation, the depicted FIGS. 2A & 2B components and functions remain essentially the same; only the various form factors and/or technology used to manufacture, connect, or assemble the components are different.

It should be noted that a particular variation of a preferred embodiment includes, for example and without limitation, a system wherein the functionality of the MPUs are emulated by the CPUs. A disadvantage of this variant is that without MPUs to perform large amounts of modal interval arithmetic operations very quickly, such exemplary system can be very slow. Due to the astronomically huge amounts of computation required for most practical artificial intelligence, machine learning, and deep learning applications, it is believed that systems characterized by essential MPU hardware, as elsewhere disclosed by Applicant, will be required to effectuate meaningful reliable machine training/learning.

In advance of particulars of the contemplated training methodology, it is to be noted that a physical abstraction of the system, via Message Passing Interface (MPI) protocol, is believed desirable and advantageous. MPI is a de-facto communication protocol standard in the high performance computing industry that abstracts the physical cluster into a conceptual paradigm for parallel computing. Moreover, in addition to the abstraction, MPI provides the mechanism necessary to realize the abstraction by managing the underlying physical cluster components.

In the MPI paradigm, individual CPU computing resources are abstracted into the concept of a process, and each process has a unique identification number. Processes may send and receive messages to each other, and messages are addressed by process identification number.

By default, an MPI application associates a process with every CPU computing resource in the cluster. For example, in a scenario wherein the cluster comprises ten computers, each with sixteen processing cores and each core supporting two hardware threads, the cluster is fairly characterized by three-hundred-twenty hardware processors, the application thusly consists of three-hundred-twenty processes. Any process can send or receive messages in relation to any other process, regardless of which hardware processor the process may actually be running on within the system. Thus, MPI essentially abstracts away all of the underlying physical details of the system in order to provide a simpler conceptual view of communication between processes. Because MPI is such a robust and well-supported industry protocol, the preferred embodiment assumes MPI is used to abstract the system as described above. However, other protocols and physical mechanisms that can provide a functional equivalent are also contemplated, the system/system operations suitably adapted.

It should be noted that MPI only abstracts the communication between CPU computing resources. The communication between CPUs and MPUs is realized by a separate mechanism. For example, with reference to the system of FIG. 2, more particularly FIG. 2A wherein the exemplary training accelerator is in a rack-mountable form factor and connected to the CPU servers via the network, the preferred mechanism may be, but is not limited to, remote direct memory access (RDMA) over Converged Ethernet (i.e., RoCE). If the training accelerator is a discrete card that connects directly to the motherboard of a CPU server via standard or proprietary bus protocols such as PCI Express, CCIX, or OpenCAPI, the mechanism for CPU/MPU communication will be defined by the electrical and mechanical engineering specifications of the protocol. Similarly, if the MPU is directly integrated on the CPU itself, the mechanism will most likely be in the form of selector signals issued to the MPU from the CPU instruction stream.

Having provided a system or system/component overview, attention is next directed to the task of finding the global minimum of an objective function using interval arithmetic, namely, the process of ascertaining model parameters via training through the supervised learning process. The aim, advantageously using modal interval arithmetic and a novel conceptualization of process virtual address space in combination with an attendant bisection indexing scheme, is to deterministically find a set of model parameters that minimizes the objective function. An overview of correct and deterministic training immediately follows, with particulars of/for advantageous, desirable and non-limiting process virtual address space allocations/use(s), a bisection indexing scheme, and interplay between, for and among each of contemplated memory components of the process virtual address space, as well as the relationship(s) for between and/or among the contemplated memory components and the bisection indexing scheme with regard to training operations/training data processing are set forth hereinafter.

Figure 3:
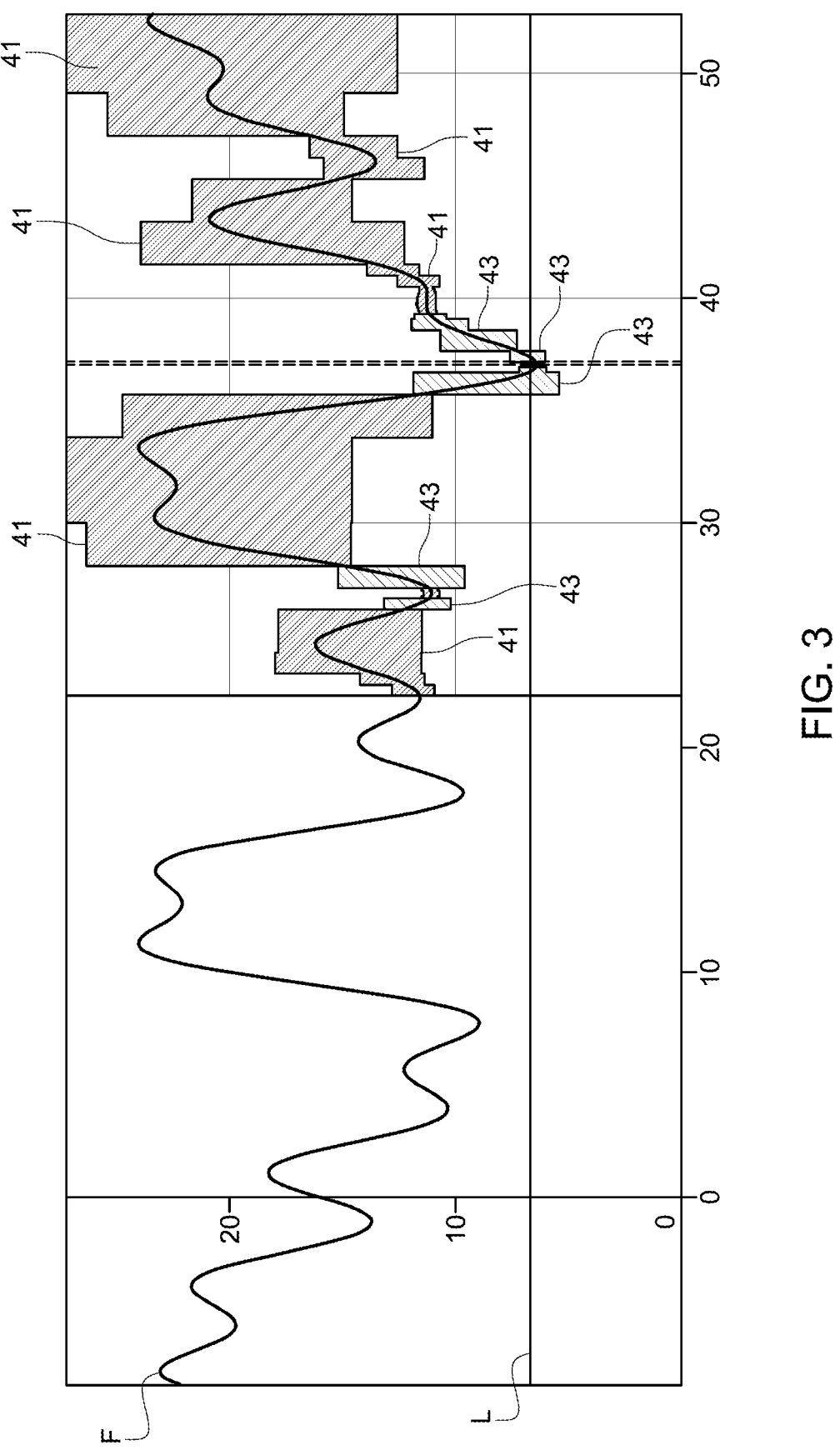

With reference now to FIG. 3, there is represented an objective function F, model training commencing with initialization of each model parameter as an interval having a lower and upper bound so that the initialized elements of the model parameters form an axis-aligned parallelotope (i.e., a "box") that defines a search region S, the horizontal axis, for the entire model parameter space. If $X \subseteq S$ is such a box, then for every X, modal interval arithmetic is used to compute an interval enclosure of the objective function.

If the minimum bound of the interval enclosure is greater than the least upper bound of the interval enclosure of any other box, as represented by the line L, this is proof that no global minimum exists in that box (e.g., areas 41), so it can be discarded/deleted. Otherwise, X is bisected into two boxes that are added to a queue and processed in subsequent iterations. This iterative process continues until a user-specified tolerance is reached or the queue is empty.

If the number of model parameters is large, which is usually the case for supervised machine learning, a naive implementation of the method described above will perform very poorly, as the computational complexity can become exponential in the number of model parameters. Developing practical implementations involves reducing the computational complexity. For example, one method widely known in the interval literature is the monotonicity test.

If the gradient of the objective function is computed with modal interval arithmetic for a box, then this is very significant, because the interval enclosure of the gradient represents information about the global topology of the objective function over the box. If any interval component of the gradient does not contain zero, this is proof that no critical points of the objective function are contained in the box (e.g., areas 43), so it can be safely discarded. Performing the monotonicity test at the beginning of each iteration has the effect of eliminating large portions of the search space that cannot possibly contain any solution, dramatically reducing computational complexity and accelerating convergence to the global minimum.

Such assessment of the model parameter space always yields correct global minimums because of the reliable and deterministic training method utilized is a "computational proof by elimination." In other words, the existence of the global minimum is proven to exist in a box that has been rigorously verified by the modal interval arithmetic to be a more optimal solution than any other. In addition to obtaining a deterministic global minimum ab initio, the need for hyperparameters is practically eliminated since the approach only requires a user-specified tolerance that indicates when the iterative bisection process has reached the desired limit.

Having set forth an overview of Applicant's interval arithmetic approach to non-linear global optimization, and made reference to a queue of yet-to-be processed box portions resulting from of the interval bisection methodology, it is to be again reiterated that the queue grows in exponential fashion. Moreover, with the model parameters numbering from $10^3$, on the low end, to $10^{12}$, and the training data commonly comprised of at least an order of magnitude more examples than trainable parameters (i.e., number of model parameters×10), the sheer magnitude of memory requirements to support reliable deterministic training is staggering and well beyond present abilities. That said, underlying Applicant's construct is the notion that each and every process in the system has its own virtual address space (VAS).

Figure 4:
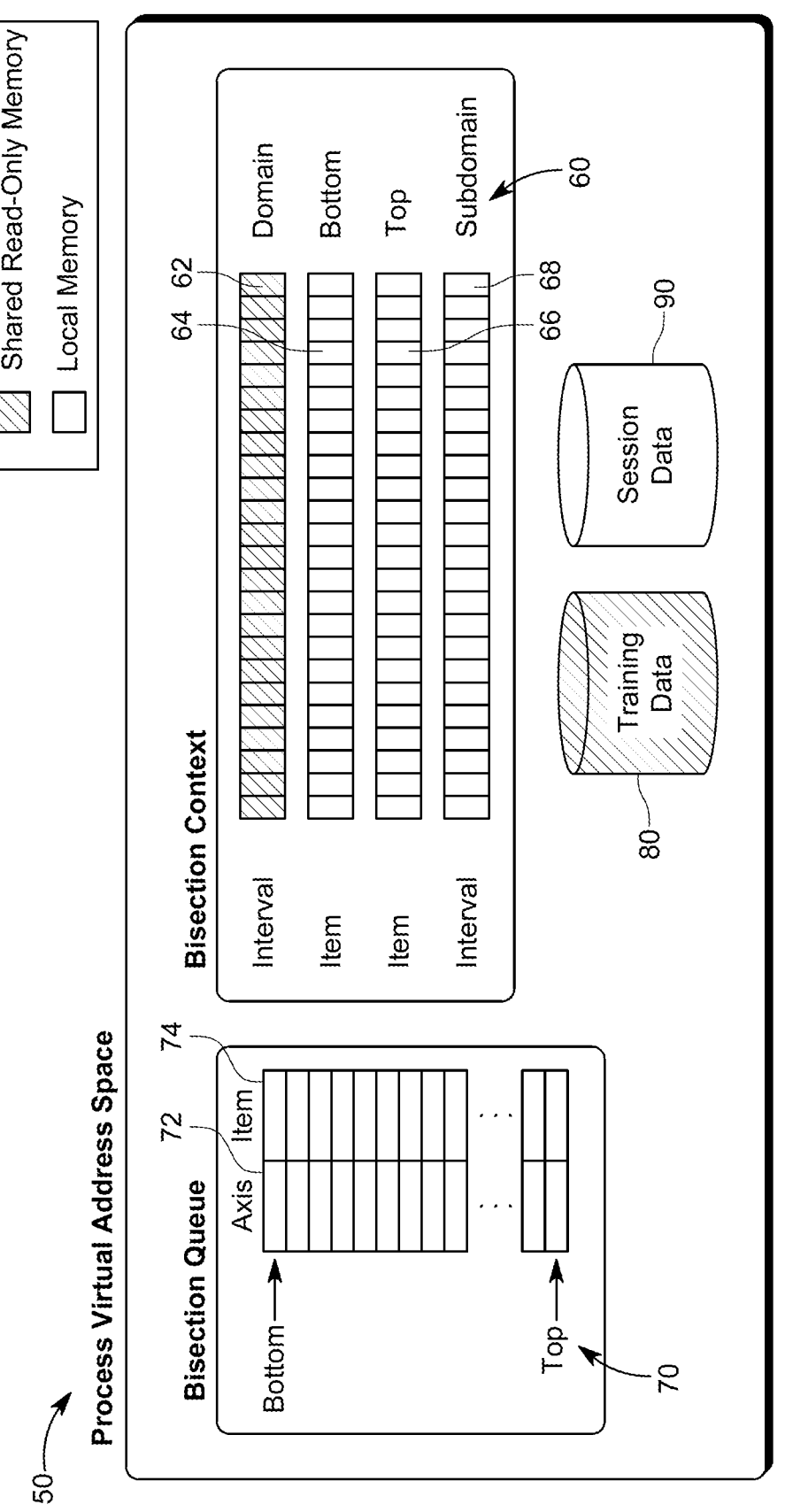

With reference now to FIG. 4, advantageous, non-limiting memory components of a process are indicated with reference to process virtual address space 50, namely, bisection context 60, bisection queue 70, training data 80, and session data 90. Bisection context is further characterized by at least four arrays, which for the sake of the instant description are named Domain 62, Bottom 64, Top 66, and Subdomain 68. Domain and Subdomain are arrays of modal intervals. Bottom and Top are arrays of integers. All of the arrays in bisection context 60 have the same number of elements, the number of those elements equal to the number of function variables, i.e., one element in each array corresponds to a variable of the function to be minimized.

Each variable of the function is initialized as an interval having a lower and upper bound, forming an axis-aligned parallelotope that defines a global search region for the entire domain $\Omega$ of the function to be minimized. Upon system initialization, the Domain array in the bisection context is initialized with this global search region so that every function variable has a corresponding interval "domain value" in the Domain array.

After system initialization, the Domain array and the training data are never modified. It is therefore advantageous, although not required, that the virtual address of these memory components be mapped to a physical memory location shared by many processes. This is easy to do on most operating systems, for example, using memory mapped files. It is advantageous because the training data, in particular, can be very large, and allowing many processes to share a read-only instance can significantly reduce the total amount of required memory. The ability to do this successfully may depend, for example, on the contemplated variations of the adopted system (i.e., one or more shown or described heretofore, or suitably adapted).

While an overview of the optimization process, wherein the global search region in the Domain array is bisected into smaller subdomains until the global minimum is proven to exist in a box found via proof-by-elimination, has been set forth with reference to FIG. 3, a hybrid parallelization method of the process is believed desirable and advantageous, and is realized in a work-stealing scheme (see e.g., Prell, *Embracing Explicit Communication in Work-Stealing Runtime Systems*, Ph.D. Dissertation, University of Bayreuth, 2016).

Each process doing work (a "worker") sends a work stealing request. All of the steal requests are forwarded amongst the processes. A process for managing the work stealing scheme (i.e., the "manager") responds to the first steal request it receives by sending the global search region in a message to the requesting worker; then the manager forwards all subsequent steal requests. Once a response to a steal request is received by a worker, the worker begins a depth-first search, placing unprocessed boxes at the top of its queue. As steal requests from other workers arrive, the worker sends messages containing unprocessed boxes from the bottom of its queue to the requesting workers. In the contemplated, non-limiting hybrid parallelization method, each worker performs a depth-first search on a different subset of the global search region. At the same time, a breadth-first search is effectively performed by the workers via the work stealing process.

For each worker, integers in the Bottom array of the bisection context represent a bisection status for the Domain array. The bisection status uses an indexing scheme to record how each domain value in the Domain array is restricted to an interval subset of itself.

Figure 5:
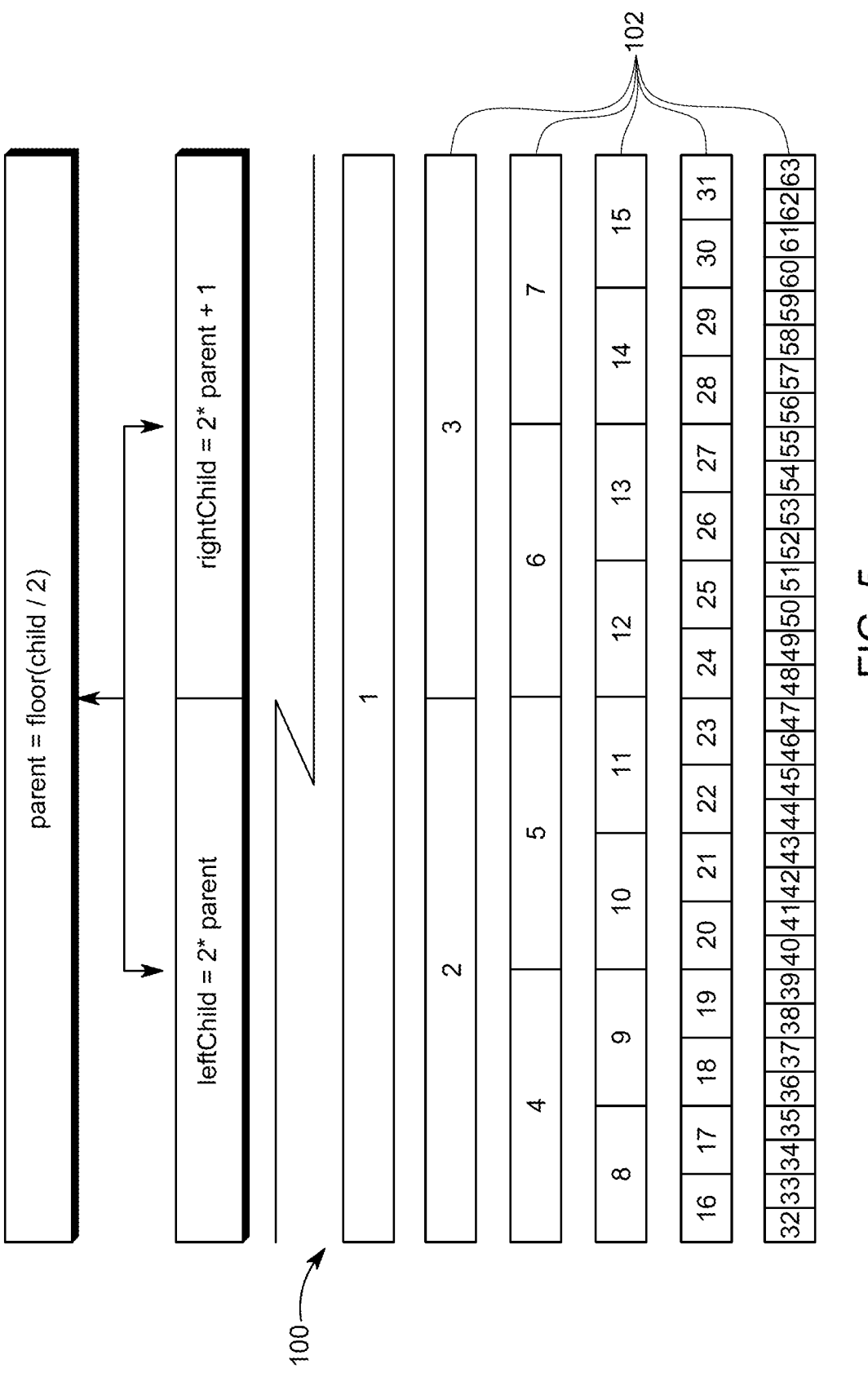

With reference now to FIG. 5, a desirable, advantageous non-limiting indexing scheme 100 for a single domain value is depicted, codes 102 representing labeled bisection item elements (i.e., one of sixty-three intervals/interval subsets), with the parent/child element relationships set forth in the upper figure portion. A positive integer (i.e., an "item") encodes which interval subset of the domain value (e.g., 1-63) is recorded in the bisection status. Root item 1 represents the entire domain value. An item i can be bisected into left child 2i and right child 2i+1; and, any item (except the root item) can recover its parent as $\lfloor i/2 \rfloor$. The "depth" of item i can also be recovered as $m=\lfloor \log_2(i) \rfloor$, and the "size" of depth m, i. e, the number of items in the indexing scheme at depth m, is $n=2^m$.

Integers in the Top array also represent a bisection status for the Domain array. However, each item in the Top array is an item that represents a subset of its corresponding item in the Bottom array. Under this restriction, the bisection status in the Top array is a subset of the bisection status in the Bottom array.

Intervals in the Subdomain array represent a subset of the global search region in the Domain array, as recorded by the bisection status in the Top array. Specifically, if i is an item in the Top array, n is the size of the depth at item i, and [a,b] is the corresponding element in the Domain array, then the corresponding element in the Subdomain array is [u,v], where $$u = a + \frac{i-n}{n} \cdot (b-a)$$

$$v = a + \frac{i-n+1}{n} \cdot (b-a)$$

The bisection queue is a collection of bisection records. Each bisection record comprises two integer fields, e.g., Axis 72 and Item 74. The Axis field is an index to a particular array element in the bisection context, and the Item field is a record associated with that particular array element. The bisection queue is a double-ended queue, so bisection records can be added or removed from the top or the bottom of the queue. At system initialization, the bisection queue is empty.

In order to support the "obnoxious case" of nonlinear global optimization using interval arithmetic when the function to be minimized consists of thousands or millions of variables (see Neumaier, *Complete Search in Continuous Global Optimization and Constraint Satisfaction*, Acta Numerica 2004 (A. Iserles, ed.), Cambridge University Press 2004), the bisection context and bisection queue act as a state machine that maintains a bisection state. The essential operations on the bisection state are Reset, Push, Pop, Remove, and Cleanup, each taken up seriatim.

The Reset operation occurs when an idle process receives work to perform. The work arrives in a message containing an array of integers that are copied into the Bottom array of the bisection context. The Reset operation assumes, as a precondition, the work has already arrived and is copied from the message into the Bottom array; the operation also requires the bisection queue to be empty. The Reset operation copies the contents of the Bottom array into the Top array, so that both arrays are identical, then updates each element of the Subdomain array as previously described.

In connection to further contemplated operations, namely, Push, Pop, Remove and Clean-up, reference is generally and broadly made to FIGS. 6A-11B. The relatedness of/for process virtual address space memory components, the parameter domain and the disclosed indexing scheme are schematically set forth as to the contemplated operations.

Figure 6A:
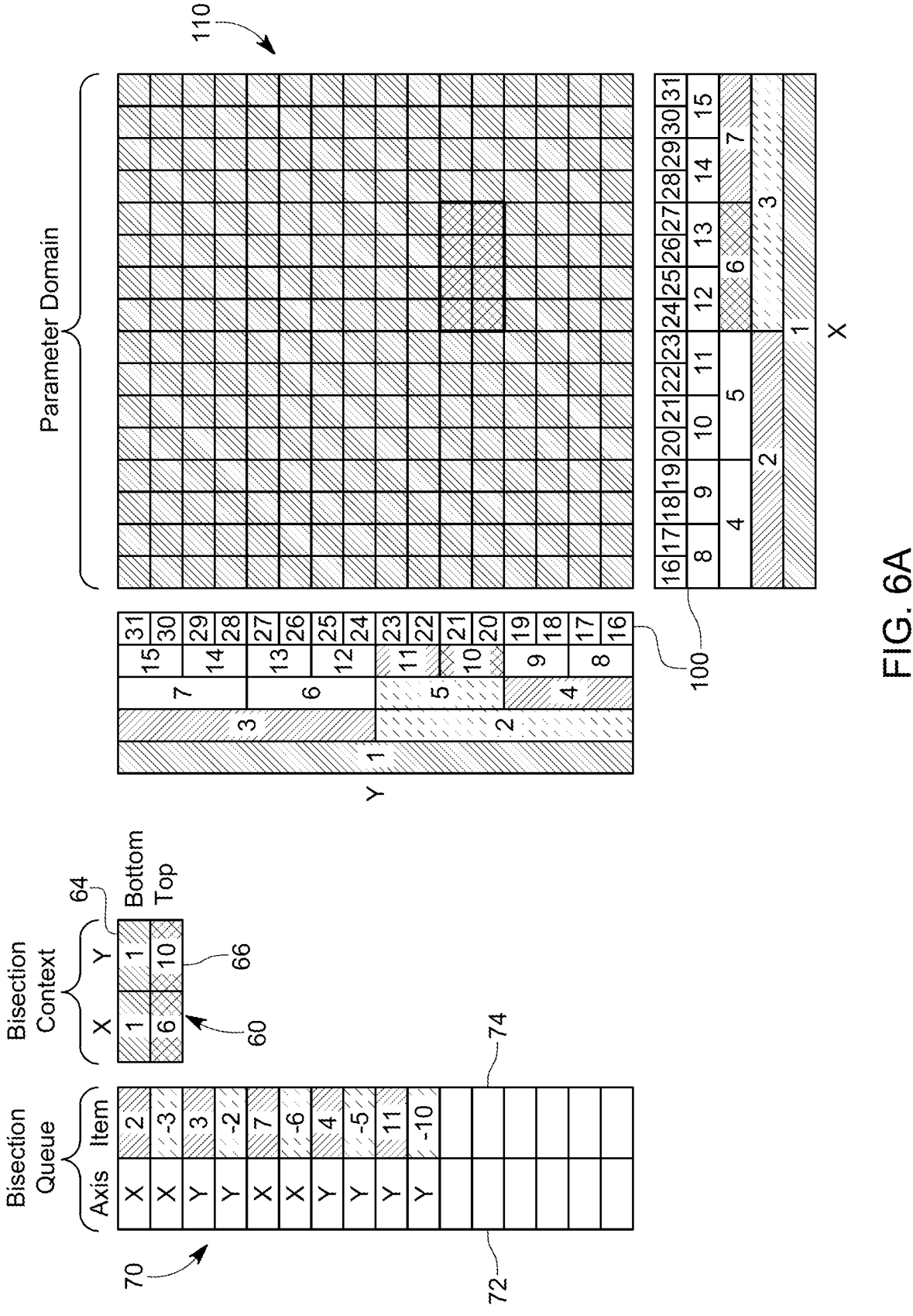
FIGS. 6A & 6B schematically depict a relatedness of/for process virtual address space memory components (FIG. 4), the parameter domain, and the indexing scheme (FIG. 5) in connection with a Push operation, namely conditions/relationships before (FIG. 6A) and after (FIG. 6B) as to the depicted operation.
Figure 6B:
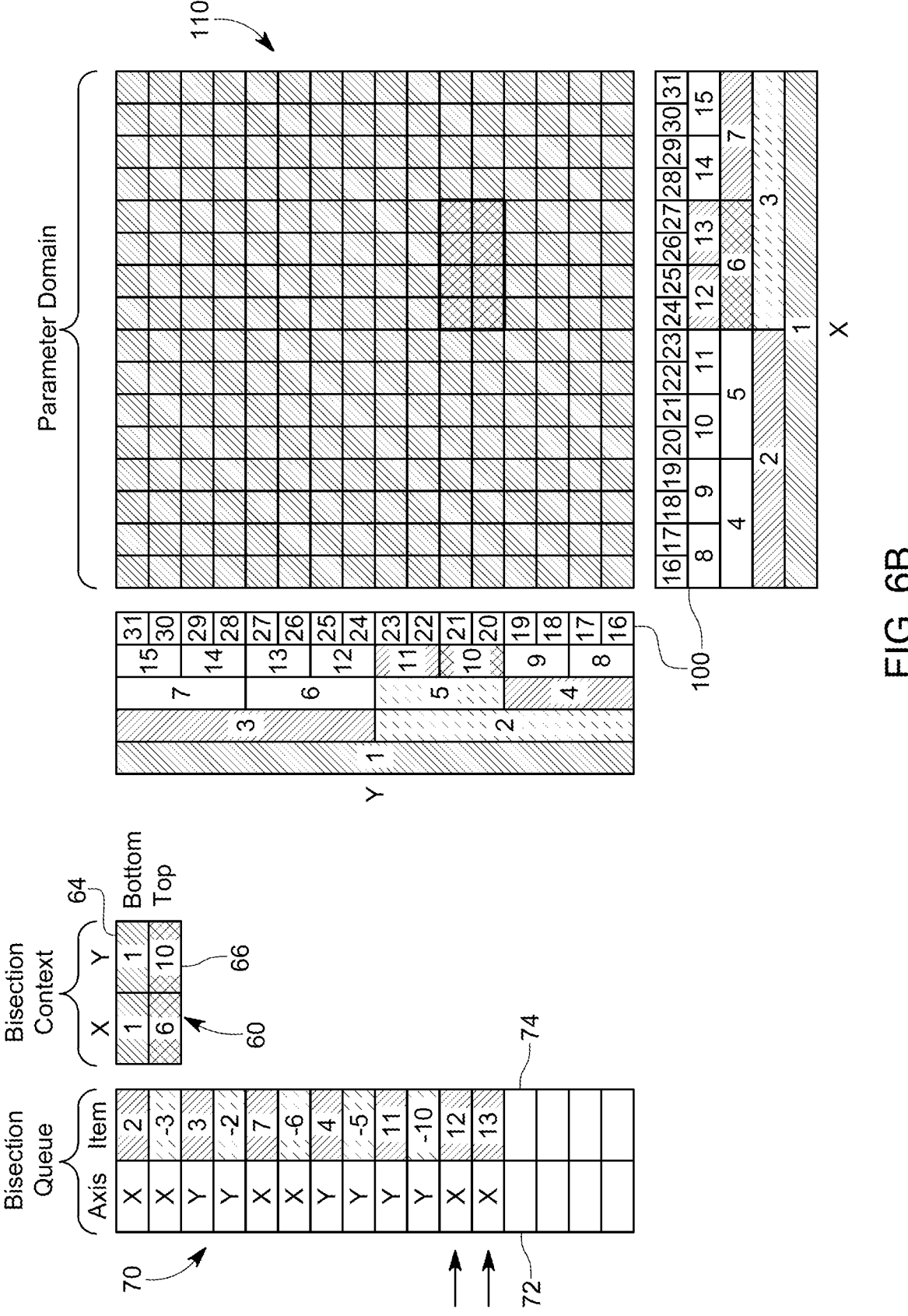

With reference to FIGS. 6A & 6B, notionally, the Push operation adds or inserts a bisection record (→) at the "top" of bisection queue 70 as is appreciated with comparison of FIG. 6A with FIG. 6B), so as to form a stack of yet to be processed intervals, more particularly, and effectively, an accumulatingly catalogued, or mapped stack of yet to be processed intervals. Two Push operations or queue additions are depicted (FIG. 6B). This operation is a depth first, stepwise, methodical descent through the interval domain bisection/domain array.

Bisection queue 70 is represented as having recorded/ memorialized the X-Y parameter domain bisections, namely, bisections corresponding to/with domain indexing scheme 100 depicted adjacent the axes of the illustrative parameter domain 110, figure right, a status of bisection context 60 likewise indicated, more particularly, elements of/for Bottom 64 and Top 66 integer arrays are correspondingly indicated.

Each queue entry is characterized by Axis 72 and Item 74 elements, the latter element being a code 102 of the indexing scheme 100 representing the bisection status for Domain array 62 of bisection context 60 (FIG. 5). As illustrated, interval subset in X parameter space, indicated by code 3, has been bisected into a subset pair characterized by codes 6 & 7 (FIG. 6A), subset "6" bisected into a further subset pair characterized by codes 12 & 13 (FIG. 6B) with parent subset "3" thereafter negated (i.e., having been processed without detection of a "solution,") the code associated with this subdomain is negated for the sake of the bisection queue (i.e., a signed negative is registered in Item field 74 of the bisection queue 70), each of those further subset pairs "pushed" for later processing (i.e., codes 12 & 13 added to ((→)) Item field 74 of the bisection queue 70.

With reference to FIGS. 7A, 7B, 8A, 8B & 8C, Pop operations are illustrated, namely, those associated with "active" and "stale" processing respectively. Notionally, the Pop operation, in contradistinction to the Push operation, is intended to be a selective ascension of/through the interval domain bisection/domain array.

The Pop operation requires, as a precondition, a non-empty bisection queue 70 (i.e., there is at least a single yet to be processed interval resulting from interval bisection). The operation contemplates the examination of the bisection record at the top of the bisection queue. As a threshold matter, the state or condition of the bisection queue element is assessed, more particularly, does the item, i.e., domain subset, have the capacity to contain a solution, or has it been determined that the domain subset at the top of the queue is not capable of containing a solution (i.e., has the Item element been negated, characterized as being stale, via representation in the item array as a signed negative code). The following description proceeds in connection to the representations of FIGS. 7A-9D.

Figure 7A:
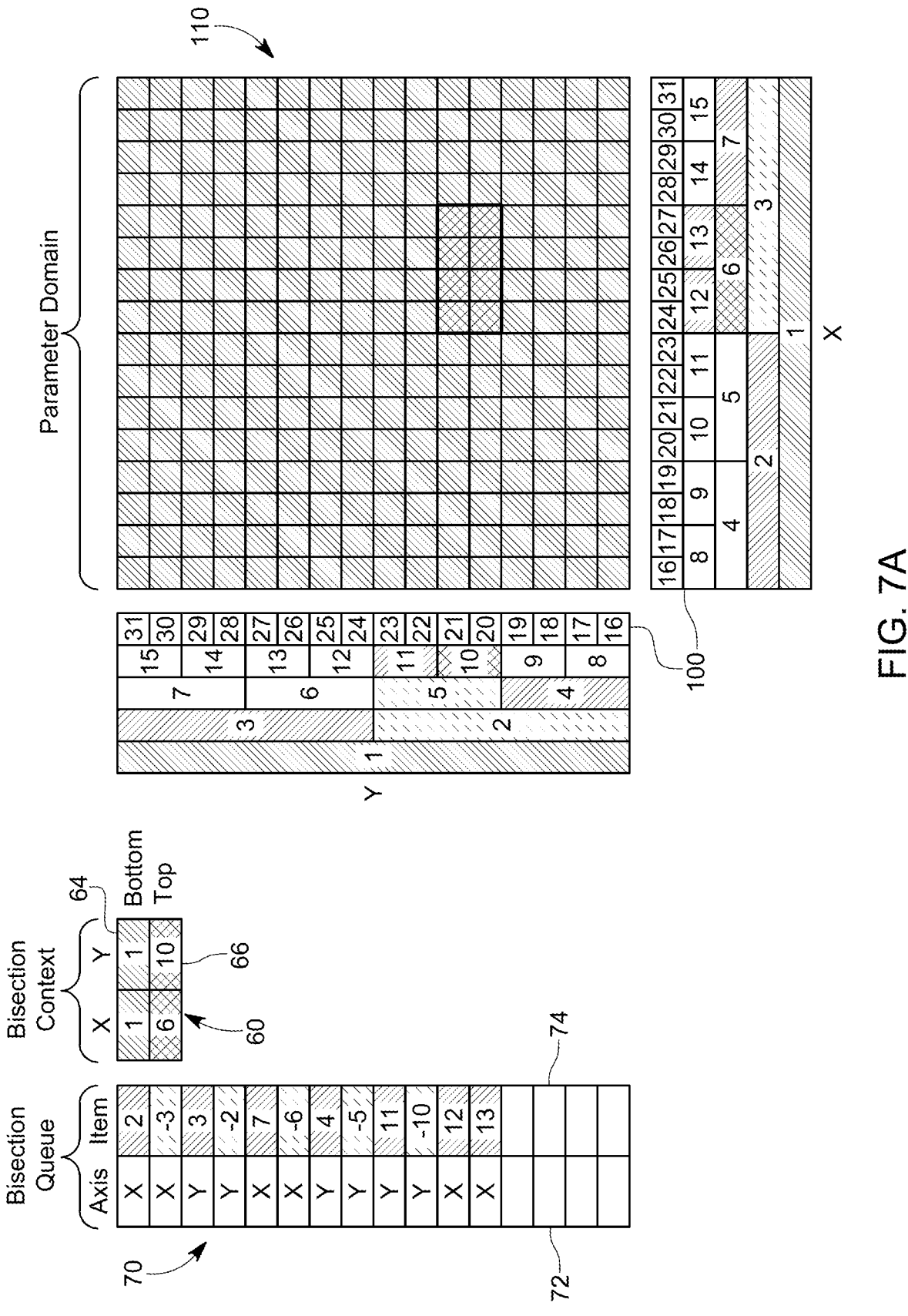
Figure 7B:
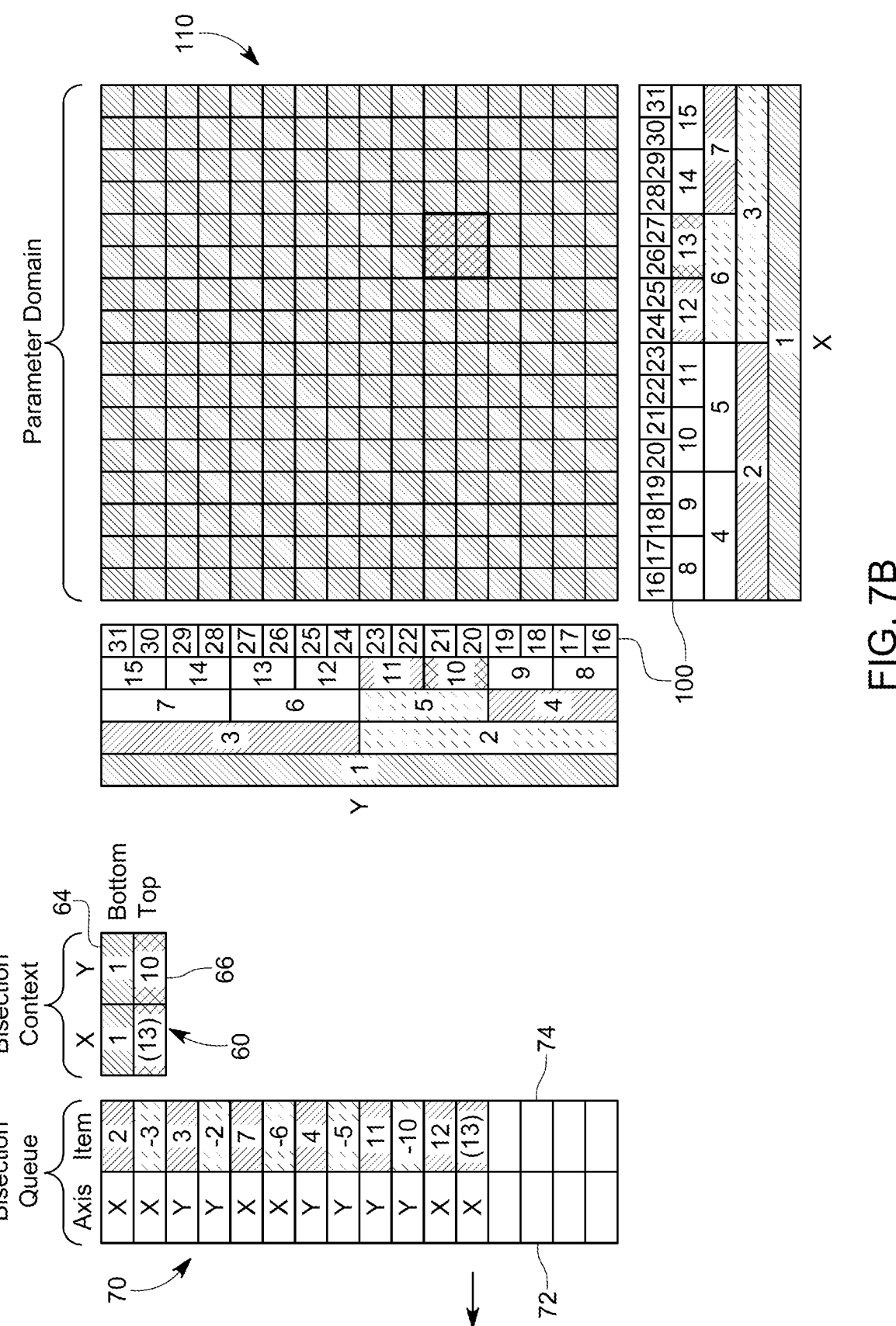
Figure 8A:
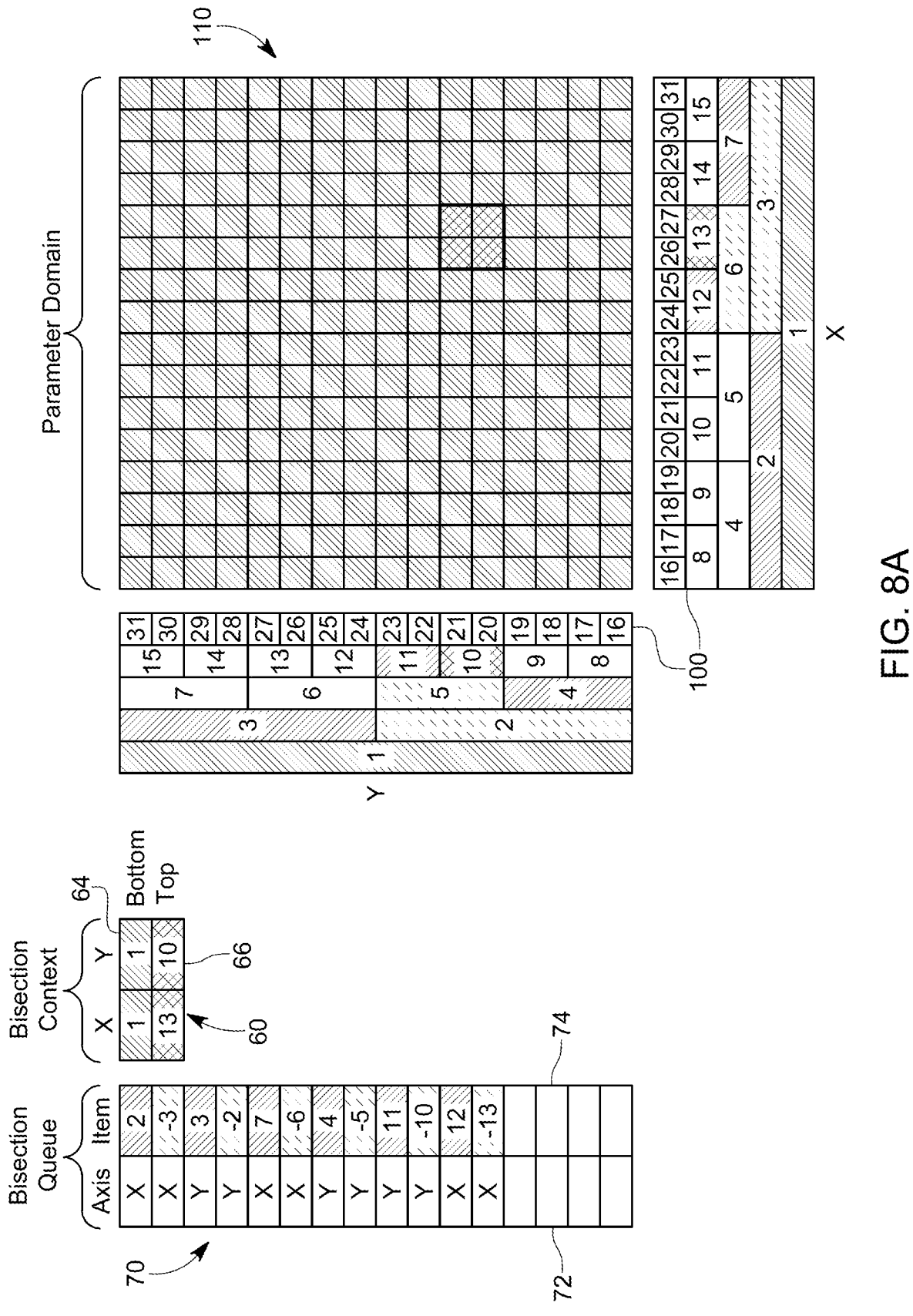
Figure 8B:
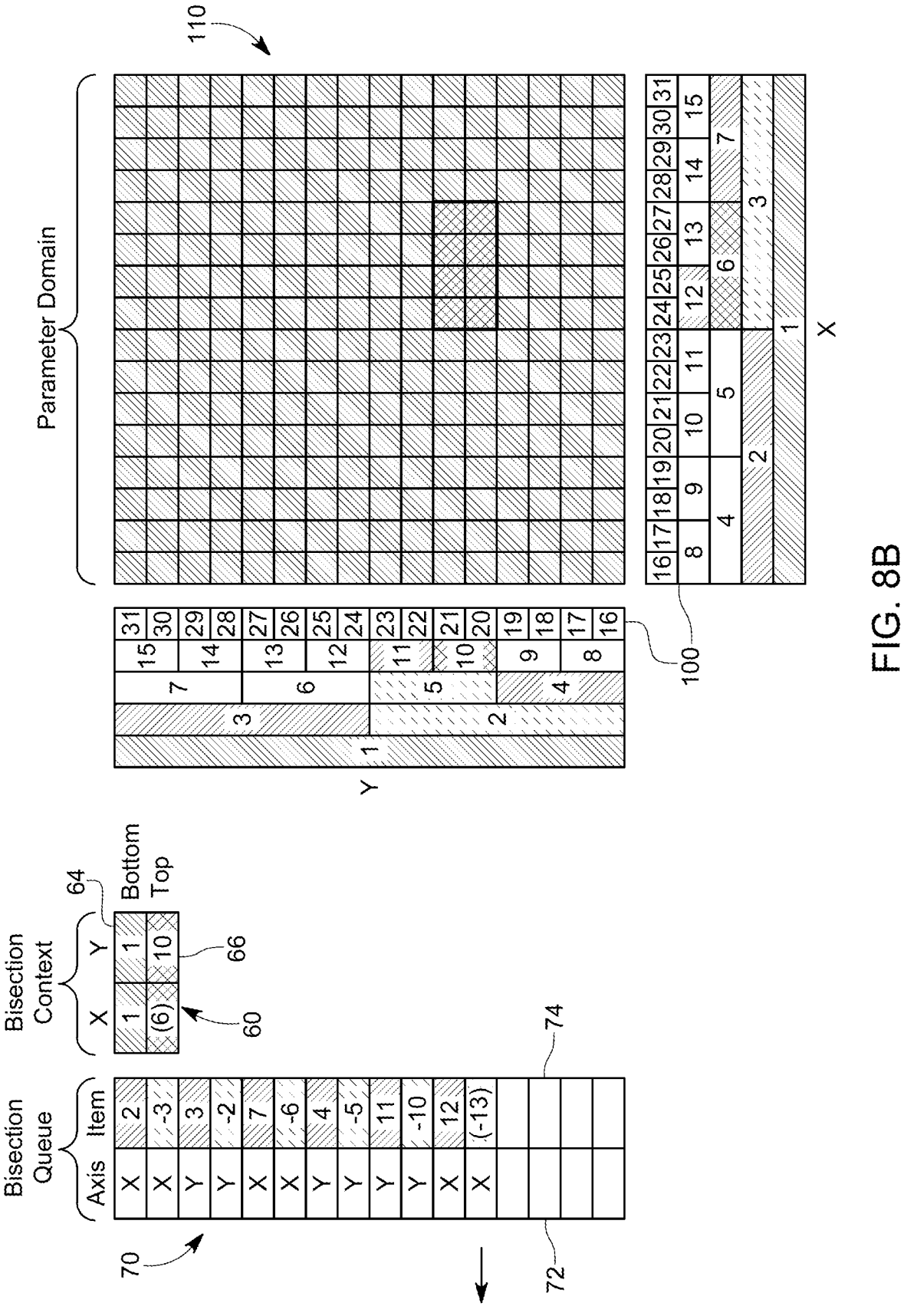
Figure 8C:
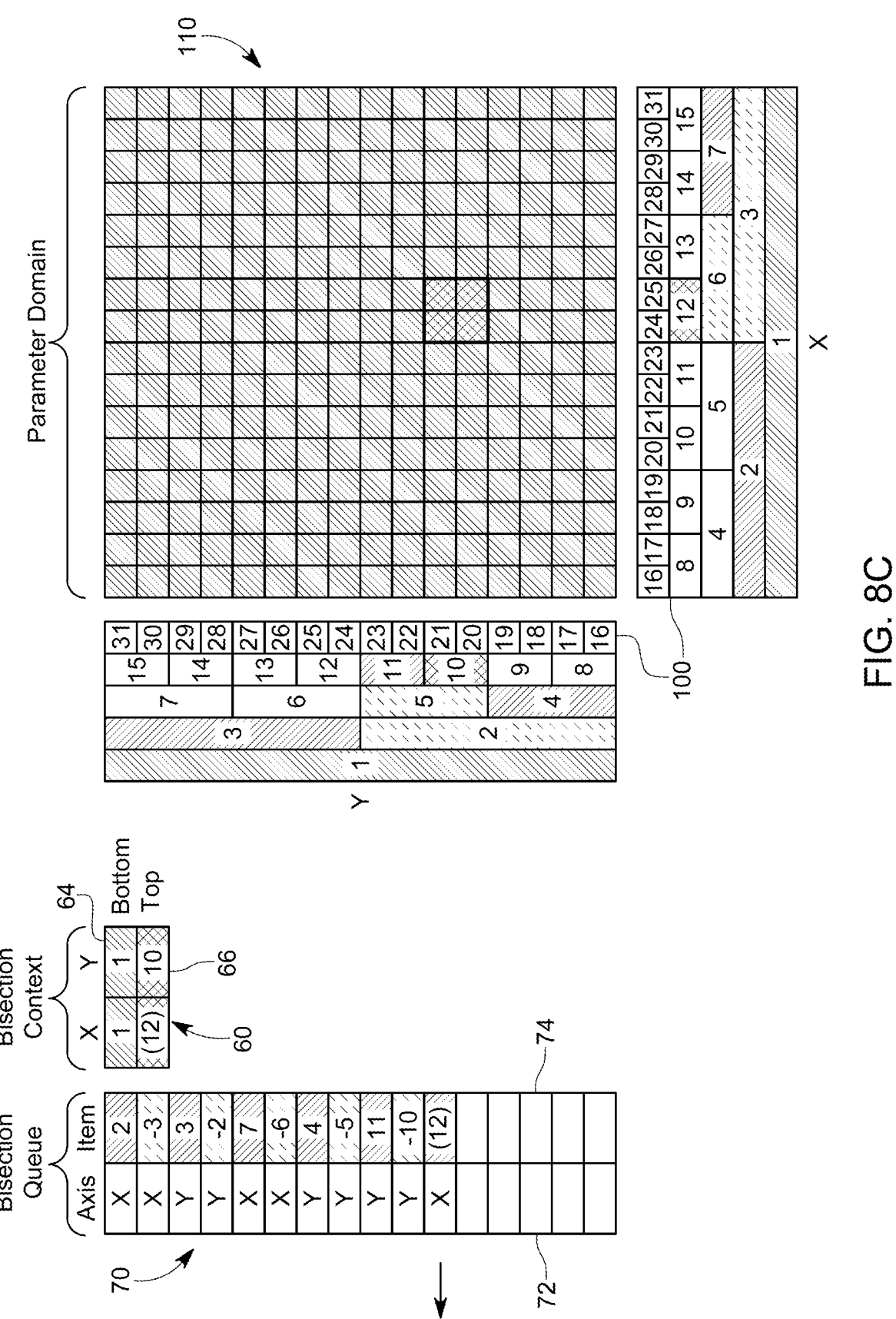
Figure 9A:
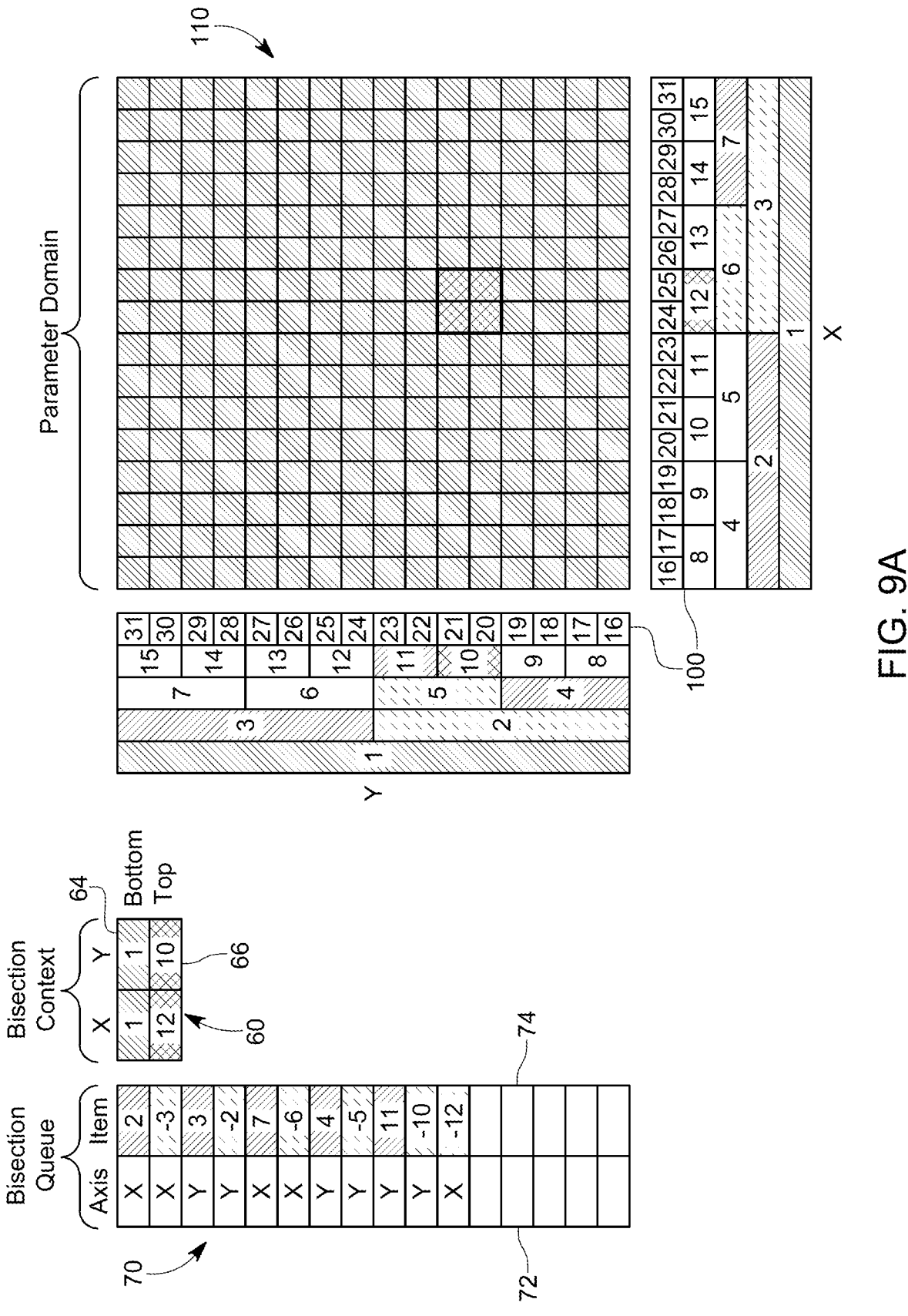
Figure 9B:
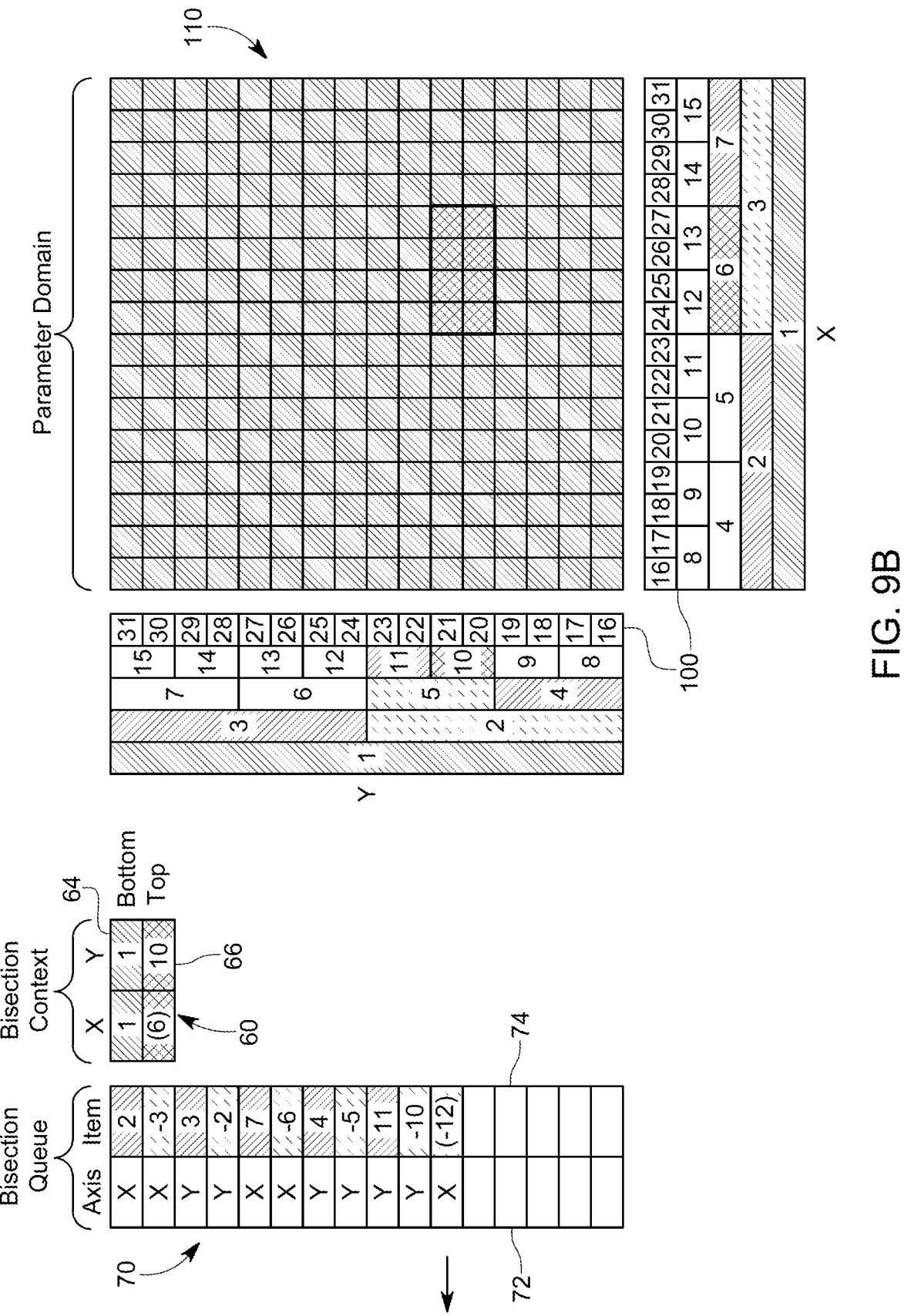
Figure 9C:
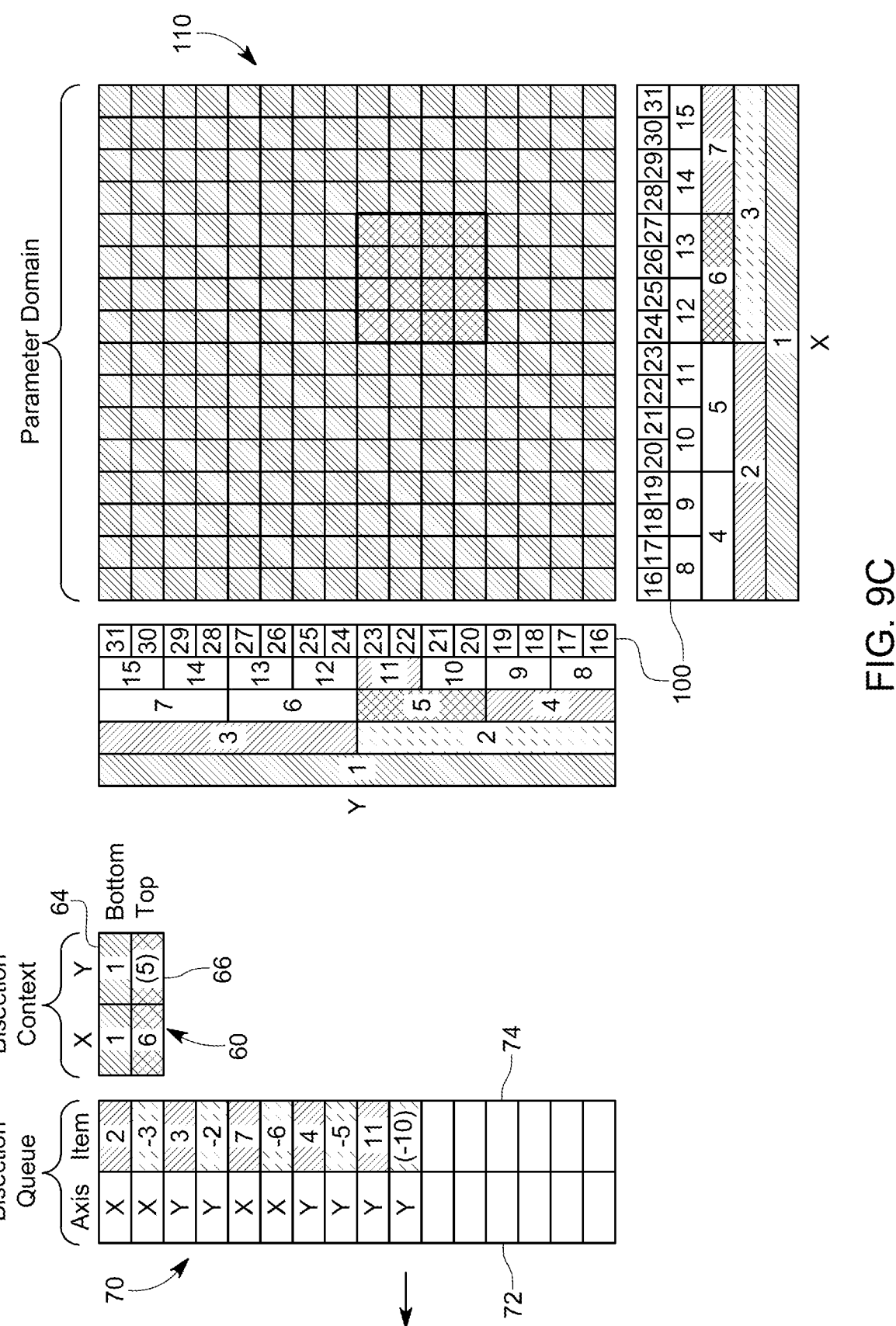
Figure 9D:
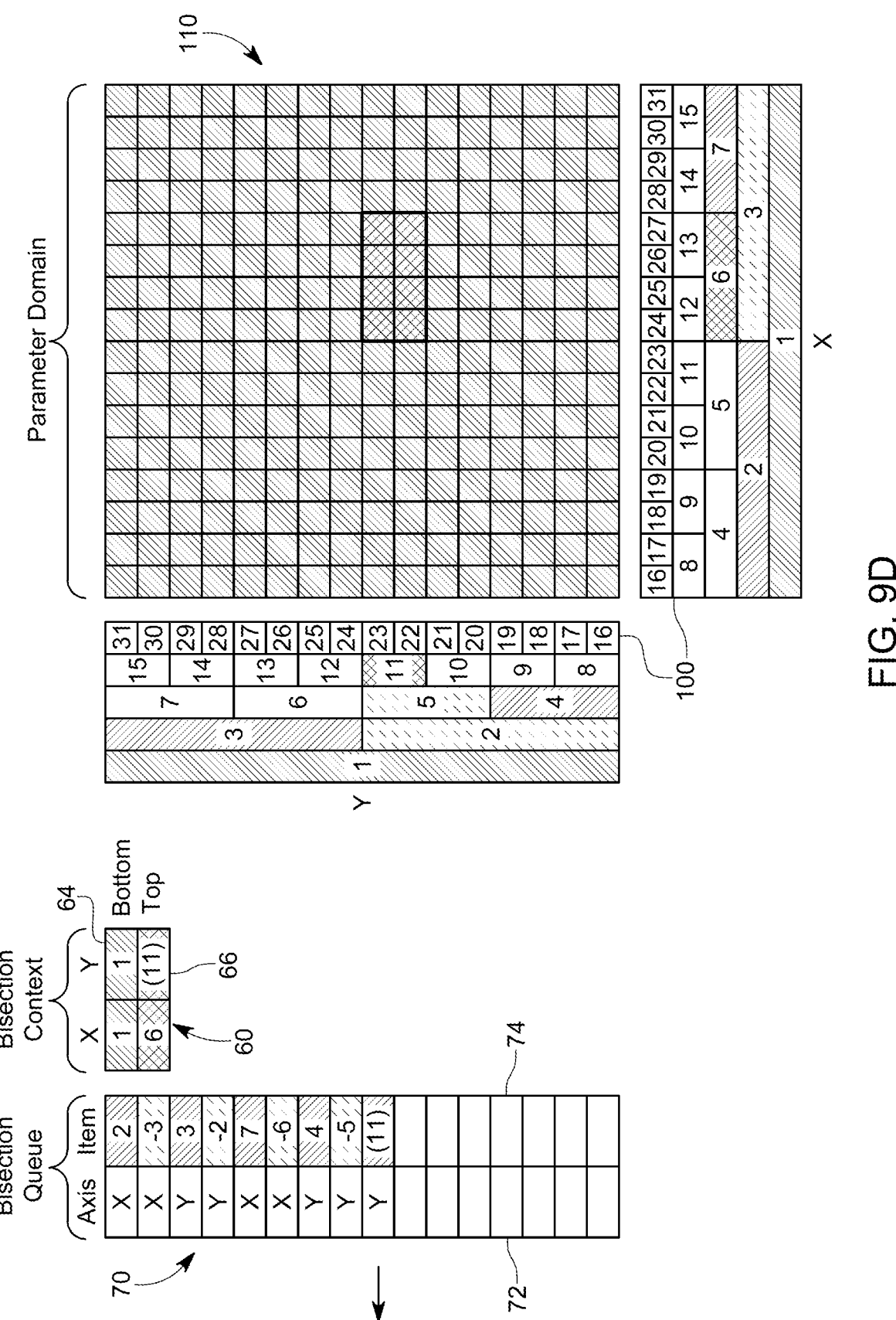

With reference to FIGS. 7A & 7B, an illustrative Pop operation is shown to the extent that Item field 74 of bisection queue 70 is not negative. As to the operation, the Item field is copied into Top array 66 of bisection context 60 at the element specified by Axis field 72. The corresponding element in Subdomain array 60 (FIG. 4) is updated, the Item field is negated (i.e., made "stale"), and the bisection record is allowed to remain at the top of bisection queue 70.

With reference to each of FIGS. 8A-9D, alternate Pop operations are shown to the extent that Item field 74 of bisection queue 70 is a signed negative code, i.e., the bisection record is "stale" and a parent item is recovered from the absolute value of the Item field. As to the operation upon the recovered parent, the code of Item field 74 is copied into Top array 66 of bisection context 60 at the element specified by Axis field 72. The corresponding element in the Subdomain array 60 (FIG. 4) is updated, the empty bisection record is erased from the top of the bisection queue, and another Pop operation is performed on the "new" top of the bisection queue.

Figure 10A:
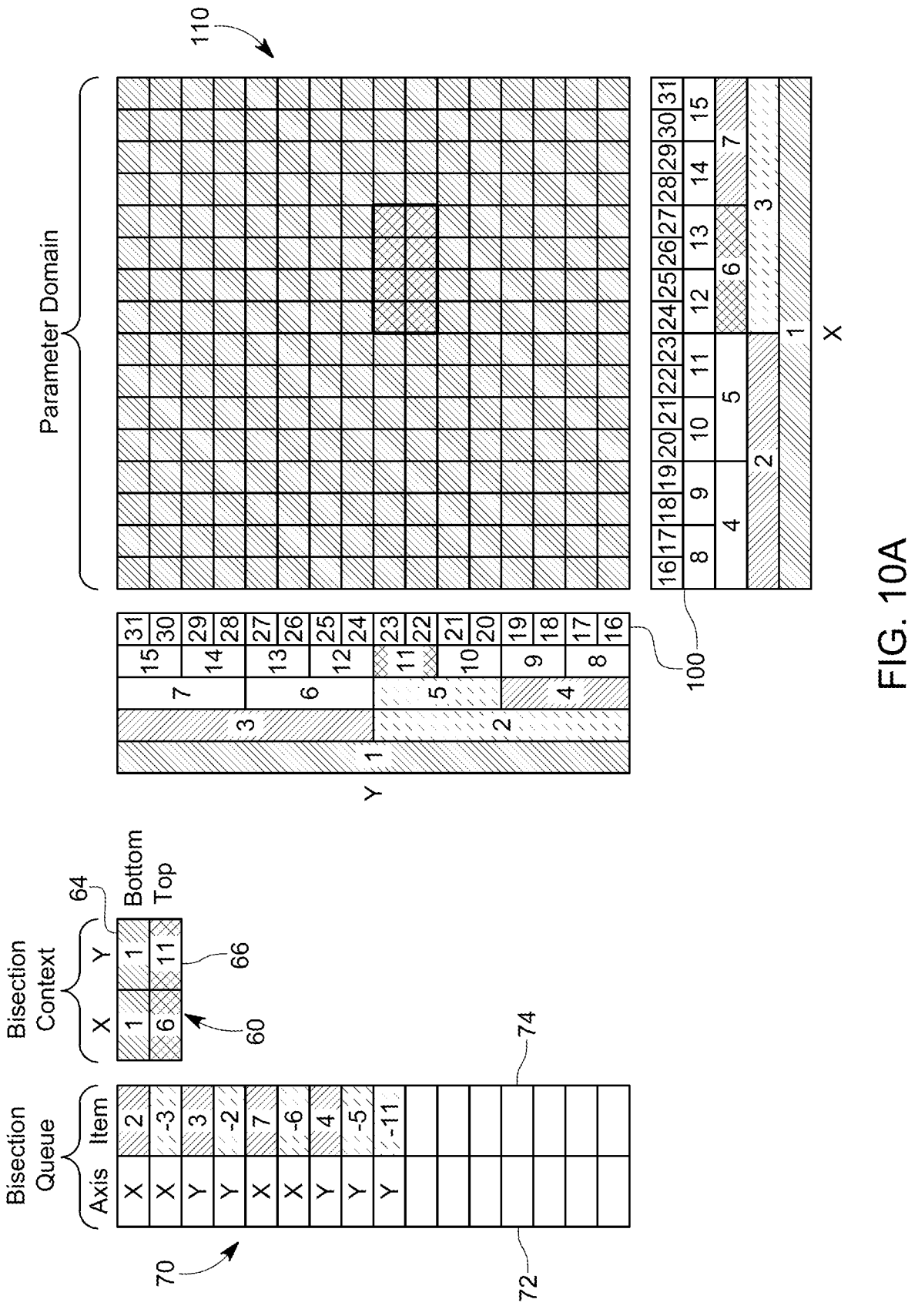
FIGS. 10A & 10B schematically depict a relatedness of/for process virtual address space memory components (FIG. 4), the parameter domain, and the indexing scheme (FIG. 5) in connection with a Remove operation, namely conditions/relationships before (FIG. 10A) and after (FIG. 10B) as to the depicted operation.
Figure 10B:
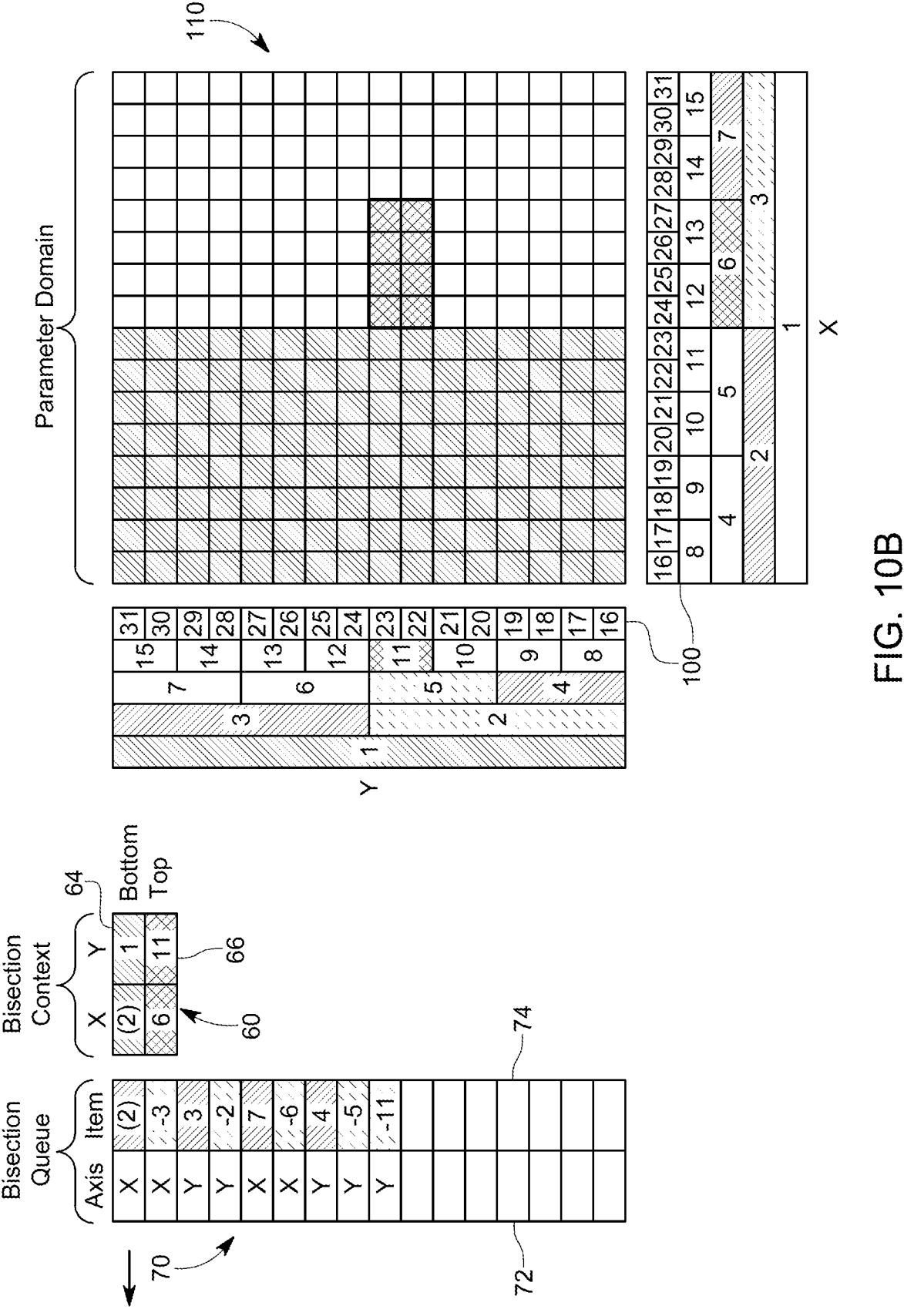

With reference to FIGS. 10A & 10B, the Remove operation requires, as preconditions, that bisection queue 70 is not empty and that the bisection record at the bottom of the queue is not stale (FIG. 10A). The Remove operation erases the bisection record at the bottom of the bisection queue after Item field 74 is copied into Bottom array 64 of bisection context 60 at the element specified by Axis field 72. Thereafter (FIG. 10B), Bottom array 64 is sent in a message to another worker of the system in furtherance of further, parallel processing.

Figure 11A:
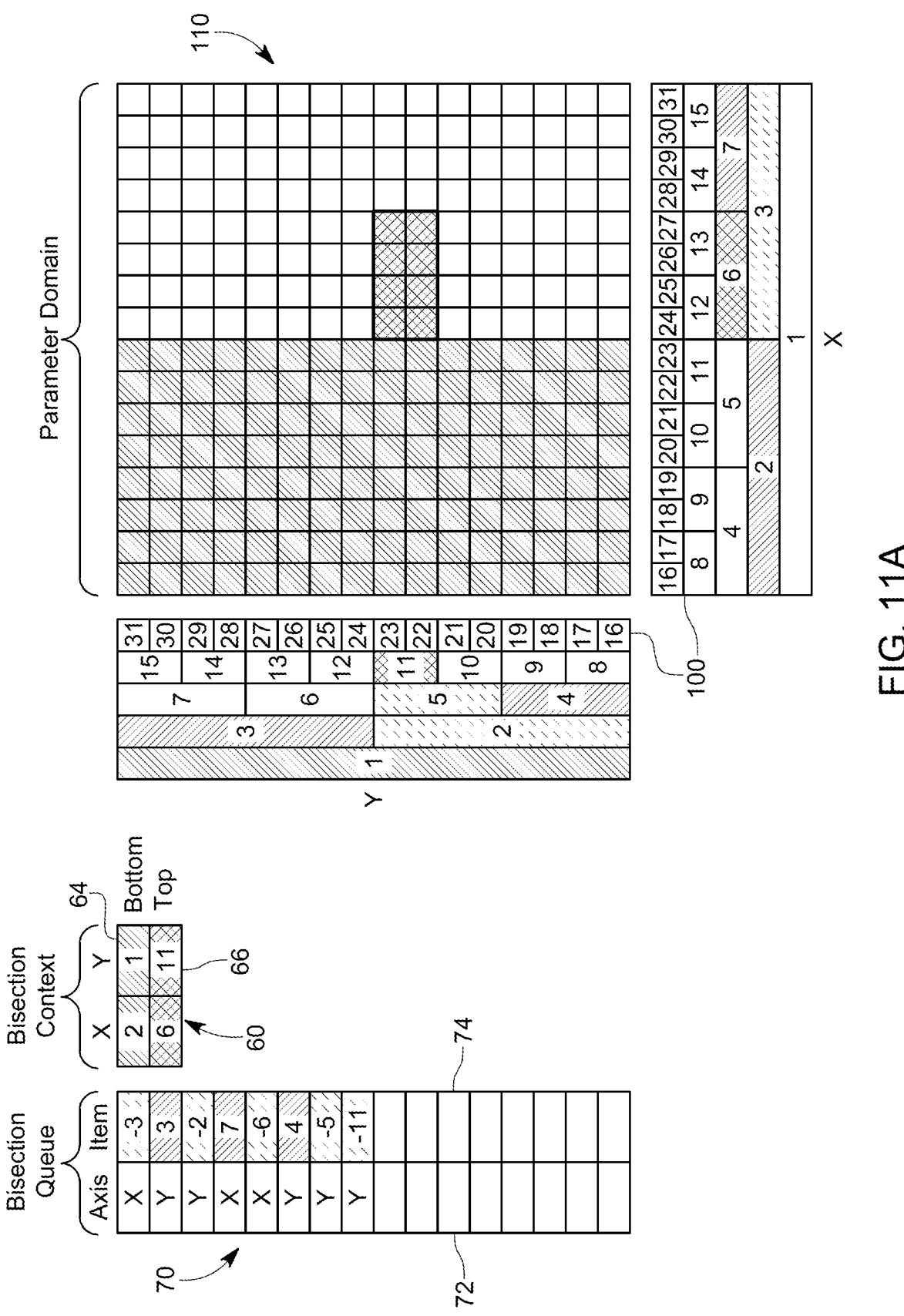
FIGS. 11A & 11B schematically depict a relatedness of/for process virtual address space memory components (FIG. 4), the parameter domain, and the indexing scheme (FIG. 5) in connection with a Cleanup operation, namely conditions/relationships before (FIG. 11A) and after (FIG. 11B) as to the depicted operation.
Figure 11B:
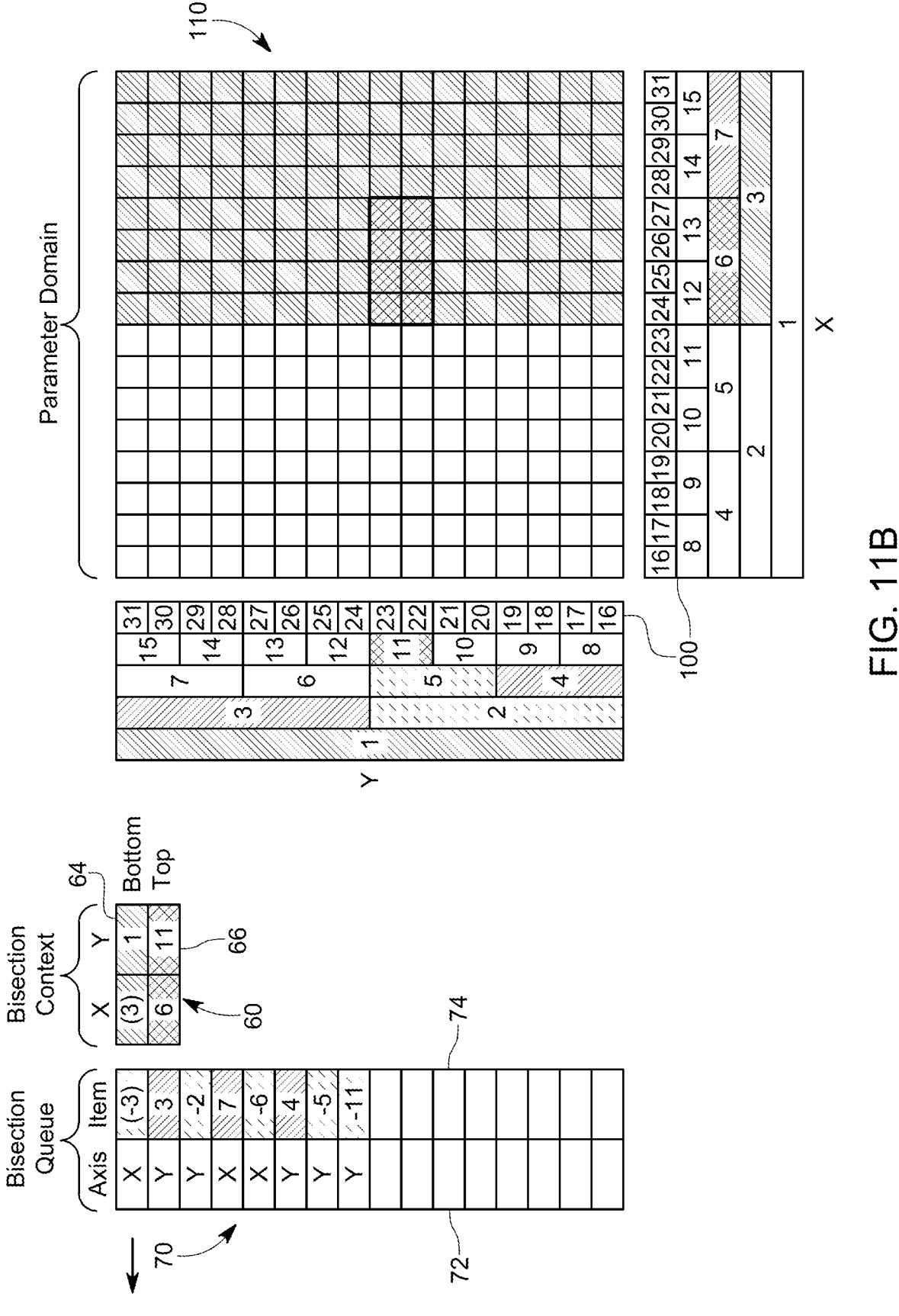

With reference to FIGS. 11A & 11B, there are represented a Cleanup operation, an operation for which there are no preconditions. If the bisection record at the bottom of bisection queue 70 is stale, it is erased after the absolute value of Item field 74 is copied into Bottom array 64 of bisection context 60 at the element specified by Axis field 72 of bisection queue 70. The operation is repeated until bisection queue 70 becomes empty, or the bisection record at the bottom of the queue is not stale. After each Pop or Remove operation is completed, an implicit Cleanup operation always occurs.

By virtue of the bisection state maintained between the bisection queue and the bisection context, the present invention only requires a fixed amount of memory for the arrays in the bisection context. A small amount of memory is also needed for the bisection queue. However, even if the bisection queue grows very large, the total amount of memory required for the bisection queue is still small owing to the size of each bisection record (two integers). Because of the bisection state, and the operations upon it, the contemplated system can perform a branch-and-bound process to solve nonlinear global optimization problems using interval arithmetic when the function to be minimized consists of thousands or millions of variables.

Having set forth at least an overview of each of the process virtual address space, a bisection indexing scheme, and advantageous contemplated non-limiting operations attendant to model parameter determination of an objective function leveraging the memory elements of the virtual address space and indexing scheme, an overview of the previously noted work stealing scheme hereinafter follows. More particularly, and contextually, a preferred, non-limiting worker and manager scheme is set forth with reference to FIGS. 12 & 13 wherein worker and manager processes and events sequence as to same are depicted, respectively.

Figure 12:
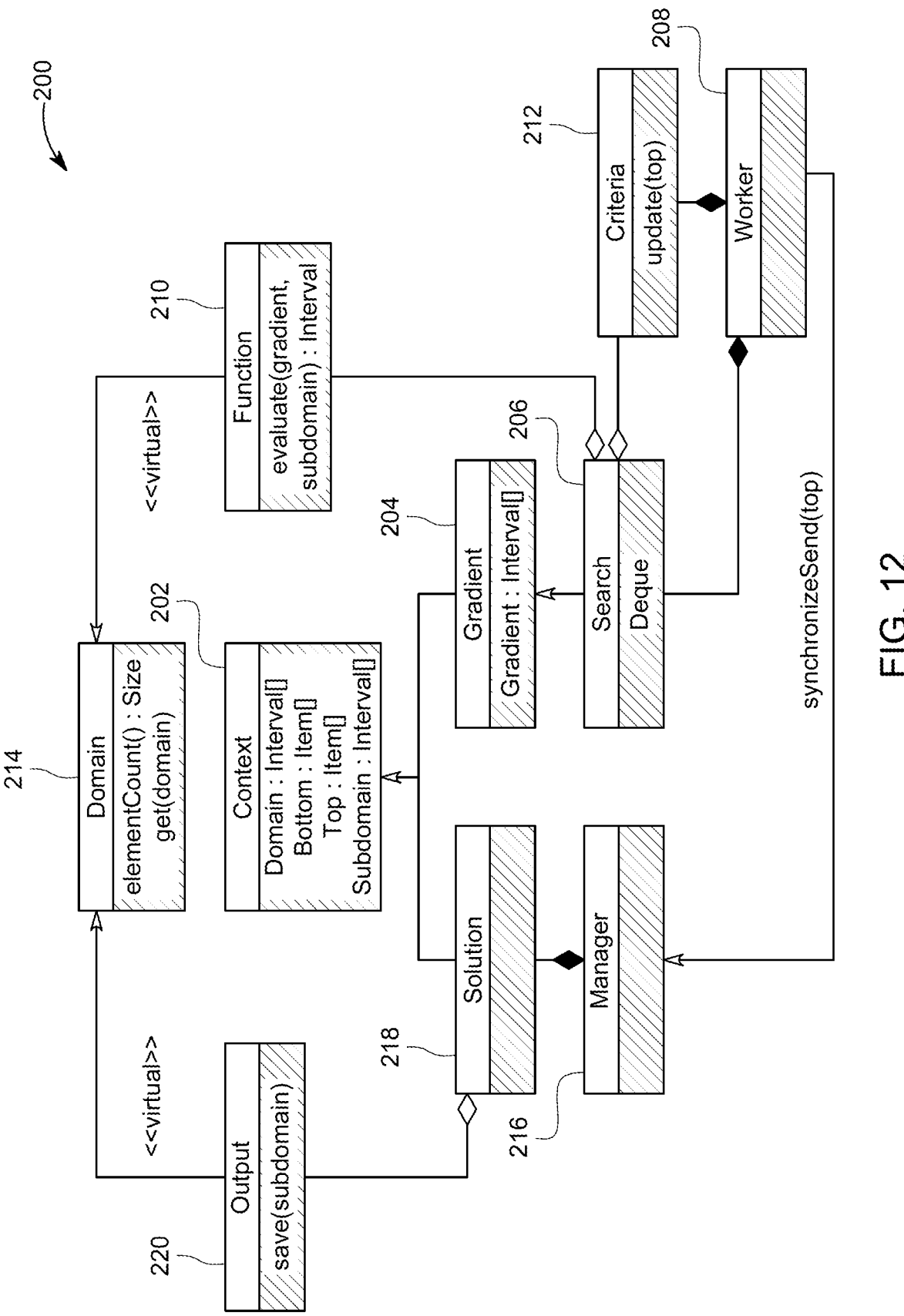
Figure 13:
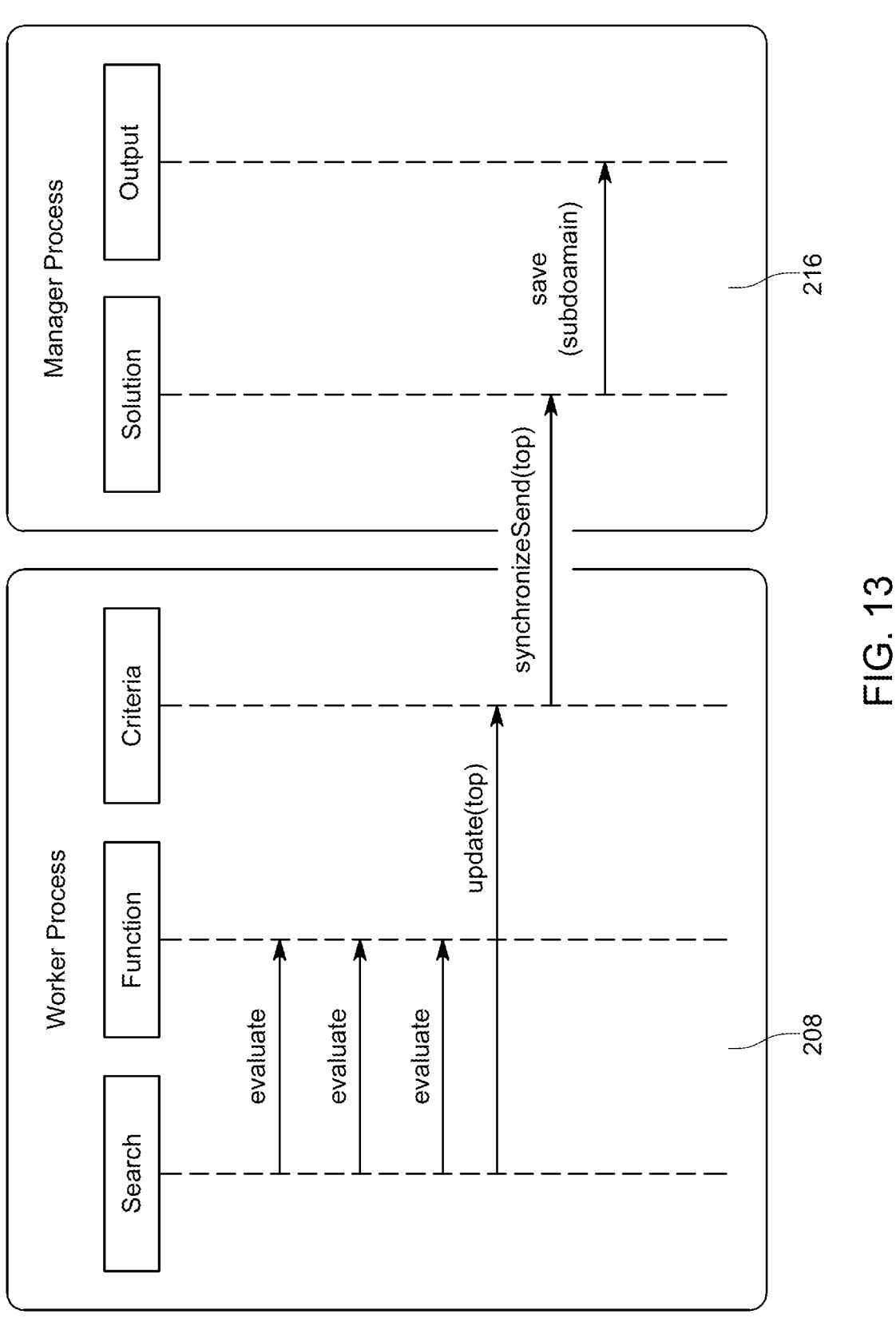

With reference to FIGS. 12 & 13, a static structure diagram of structure 200 associated with an advantageous worker and manager processes is depicted. A monotonicity test can significantly improve the overall performance of the optimization process. This requires calculating interval bounds on the gradient of the function. Context 202 is the base class for bisection contexts, and Gradient 204 is a derived bisection context. Gradient 204 includes an additional array of intervals in the bisection context for the gradient of the function to be stored in. Search 206 is derived from Gradient 204, and the Search bisection context adds the notion of the bisection queue.

All of the worker processes in the system (Worker 208) own a unique instance of Search class 206. At system initialization, the Search class is instantiated with references to the Function 210 and Criteria 212 interfaces. The elementCount method in the Domain 214 base class returns the number of function variables, which can be used to dimension arrays in the bisection context. Function 210 provides the evaluate method, which accepts a pointer to the Gradient and Subdomain arrays, evaluates the function based on the current state of the variables in the Subdomain array, updates the Gradient array, and returns an interval bound on the range of the function. Criteria 212 provides user termination criteria and the update method, which accepts a pointer to the Top array. The update method is invoked by Search 206 whenever a new local minimum is found.

There is one manager process in the system, namely Manager 216. Manager serves double-duty by receiving messages from workers that invoke the update method (see FIG. 13; worker process 208' and manager process 216'). The Top and Subdomain arrays of Manager's bisection context store the best local minimum found by all of the workers; and, the Bottom array stores the bisection state of the global search region, which is specified during system initialization. This is why Manager owns a unique instance of the Solution class 218, i.e., since Manger never requests work, it does not need a Gradient array in the bisection context, nor a bisection queue. Manager invokes the save method of the Output interface 220 each time a new best local minimum is received from a worker.

Under normal conditions, the update method is invoked very infrequently because a large amount of computation is typically required by a worker to find a new local minimum. This means that synchronization caused by multiple workers attempting to update the manager is, almost without fail, never a practical performance issue, even in a system with hundreds or thousands of workers.

The evaluate method is the essential connection point between CPUs and MPUs in the system, as the method invokes an evaluation of the function. In the context of artificial intelligence, machine learning, and deep learning, the function being minimized is a loss function defined by the training data and the artificial neural network. In "big data" applications, the amount of training data can be gigantic. It is not uncommon that a single invocation of evaluate may result in trillions or even quadrillions of modal interval arithmetic operations. For this reason, a preferred embodiment of the system is characterized by hardware MPU circuits capable of performing large amounts modal interval arithmetic operations very quickly, preferably in a single instruction, multiple data (SIMD) format and performance factor.

Additionally, evaluation of the artificial neural network, especially its gradient, often requires session data (see FIG. 4), which is memory reserved for storing intermediate calculations used in the evaluation of the artificial neural network. As mentioned earlier, the training data is read-only. This provides an opportunity to store the training data in a physical memory technology that is optimized for read-only access, and for a single copy of the training data to be shared amongst several processes. Session data, on the other hand, must be writable; and, unlike the training data, session data cannot be shared amongst processes. Each worker requires its own session data.

Because evaluation of the function is generally a very computationally intensive process, the hybrid parallelization method which has been described herein is coarsely parallel. In fine-grained parallelism, the total amount of time to complete each task is usually very small. This places unique demands on the work stealing process, often requiring a "steal-half" scheme wherein a worker responds to a steal request by sending as many as half of its queued tasks in keeping with the earlier cited work of Prell.

In coarse-grained parallelism, the time to complete each task is lengthy; and, the "steal-half" scheme usually adds little value because the default level of parallelism is already very high. Indeed, the present invention generally performs very well without using a "steal-half" scheme. This is why in the description of the preferred embodiment, workers respond to steal requests by sending only the bisection state associated with the bisection record at the bottom of the bisection queue. However, it is also contemplated that workers could respond to steal requests by sending N bisection states associated with N bisection records in the bisection queue.

Last but not least, communication of a least upper bound between workers is contemplated. Again noting that the least upper bound (the "LUB"; see/cross reference L, FIG. 3) is a conservative estimate of the best local minimum found so far, and although the LUB is just a single number, it plays a very important role in the "proof by elimination" method of the branch-and-bound process. The LUB is used as a threshold to determine which subsets of the global search region can be discarded. As the LUB becomes a more refined estimate of the true global minimum, greater amounts of the global search region can be discarded. This reduces the total amount of work needed to find the global minimum, speeding up the total amount of time required to find the global minimum.

If the LUB is shared amongst all of the workers, dramatic speed improvements can be gained. The reason for this is that when a worker improves the estimate of the LUB, all of the other workers can delete any queued bisection records which can be proven to be associated with a bounded range of the function that is strictly greater than the LUB. The ability to delete queued bisection records can grow exponentially in the number of workers, leading to a super-linear speedup. This is highly advantageous, because it means the speedup multiple grows faster than the multiple of workers.

Modern MPI implementations support remote direct memory access (RDMA), a direct memory access from the memory of one computer into that of another without involving the operating system on either computer. This permits high-throughput, low-latency networking, which is especially useful in massively parallel computer clusters. For example, the MPI_Fetch_and_op command allows a process to update a 32-bit or 64-bit memory address of another process, even if the other process is running on another computer across the network.

This mechanism is used for communicating the LUB between processes, with a very simple background data dissemination protocol (e.g., the "gossip protocol"). A copy of the LUB is stored in each process as a 32-bit or 64-bit value. As each worker processes the bisection records in its bisection queue, the worker reads and writes its own local copy of the LUB. Periodically, the worker (i.e., the "origin") will also use the MPI_Fetch_and_op command to update the LUB of a select group of other workers (i.e., the "target group"). As a result, each worker in the target group (i.e., the "target") has its LUB overwritten by the LUB from either the origin or the target, whichever has the lesser value. In other words, the minimum LUB is propagated from the origin to each target in the target group. Each target will periodically do the same thing, propagating the minimum LUB to a different target group of workers, and so on.

The parameters of the gossip protocol are twofold. One parameter is the minimum amount of time that must elapse before a worker will attempt to propagate the LUB to its target group. The other parameter is a selection of workers for all of the different target groups. Many methods of selection are contemplated, including, but not limited to, random selection, nearest physical topology, and nearest virtual topology.

By using RDMA and a simple background data dissemination gossip protocol, network communication is minimized and synchronization bottlenecks are eliminated, with high probability that the best estimate of the LUB will eventually propagate to every process in the system. Since each worker is constantly improving its own copy of the LUB, it does not hurt the reliability of the overall optimization process if there is possibly a better LUB found by another worker that it cannot see. The system only stands to gain the advantage of reducing the total amount of work, and thus increasing the overall speedup, if the better LUB is eventually propagated to all of the other workers.

As has been established, Applicant departs from minimizing the objective function $f$ with statistical machine learning methods, such as gradient descent, and instead utilizes an interval analysis method that initializes each unknown model parameter as a modal interval with a lower and upper bound. Thus, the initialized unknown model parameters form an axis-aligned parallelotope (i.e., a "box") that defines a search region S for the unknown model parameter domain $\theta$ of the global optimization problem. Then, the search region S is recursively bisected into non-overlapping subdomains, wherein each subdomain X (i.e., $X \subseteq S$) is also represented as a box; and, after each bisection, the objective function $f$ is evaluated for each subdomain using modal interval arithmetic, i.e., a subdomain X is provided as input to the objective function, and modal interval arithmetic is used to evaluate a modal interval $Y=f(X)$ for the objective function. If the lower bound of Y is strictly greater than the least upper bound computed for any other subdomain, it is a set-theoretic proof performed inside the computer that no global minimum can possibly exist in X, and X is safely deleted; otherwise, the recursive bisection process continues until an interval solution X* to the global minimum is found.

By virtue of the systems, processes, and methods set forth supra, each element of the interval solution X* obtained by the interval analysis is a modal interval [a,b] delimited, respectively, by left and right endpoints a and b, and each modal interval represents a set of real numbers defined as $$\{\varphi \in \mathbb{R} : \min(a,b) \le \varphi \wedge \varphi \le \max(a,b)\}.$$

Additionally, since X* is a subset of $\theta$ and the global minimum x* is guaranteed to be an element of X*, the implication $x^* \in X^* \Rightarrow x^* \in \theta$ will always be true. Having obtained the interval solution X* thusly, it is further utilized or leveraged in furtherance of obtaining an explanation as per the methodology of FIG. 14.

Figure 14:
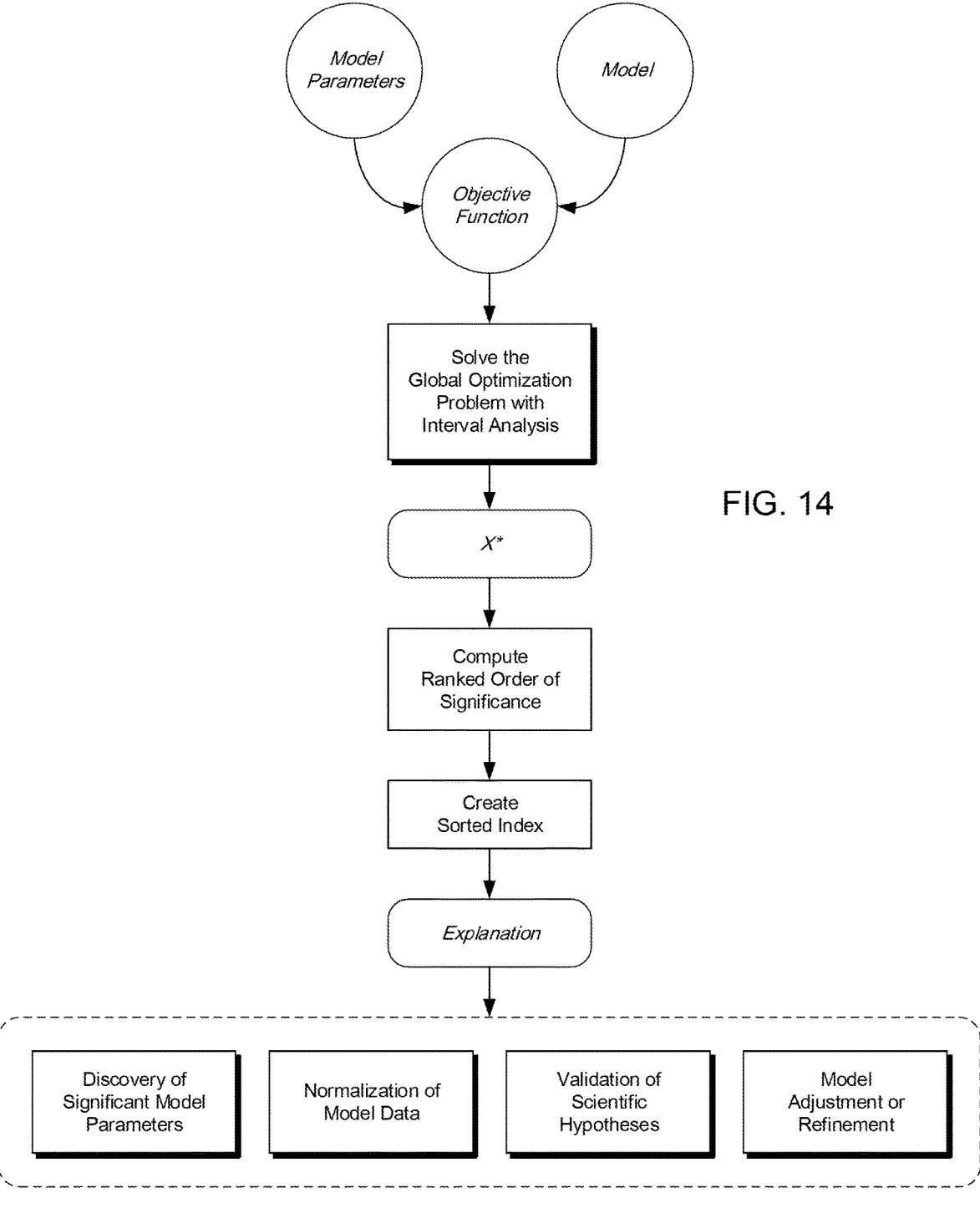

With reference to the explainable AI methodology depiction of FIG. 14, the interval solution X* is provided as input, in a suitable format, where each element of X* is delimited as a solution interval [a,b] comprised of left (e.g., first) and right (e.g., second) endpoints a and b, respectively, and each model parameter of the artificial neural network (or, more generally, the model) corresponds to a unique solution interval in X*.

The format is an encoding scheme that specifies how numeric values are represented in the memory of a computer. The preferred embodiment uses any format from the IEEE 754-2019 standard, but other formats are likewise contemplated.

For each solution interval [a,b], a ranked order of significance relative to all other solution intervals is advantageously derived by obtaining the absolute value of the difference between a and b, i.e., the "distance" between a and b, formulated as |a−b|. Because each solution interval was computed from a bisection process during the interval analysis, it may be further advantageous to derive ranked order via a logarithmic treatment of the distance of the solution interval, e.g., by obtaining the negative binary logarithm of the distance between a and b (i.e., $-\log_2(|a-b|)$). Via this logarithmic methodology, the ranked order of significance computed for all of the solution intervals shares a common linear unit. While advantageous non-limiting ranked order significance determinations have been set forth, it is to be understood that other means of deriving the ranked order of significance for each solution interval may be suitable, notionally, any and all are advantageously predicated upon the "distance" (i.e., magnitude) between endpoints a and b of the solution interval.

After the ranked order of significance is computed for every solution interval, all of the model parameters may be sorted. Each model parameter is sorted as a function of the ranked order of significance computed for its corresponding solution interval, producing an output that effectively orders every model parameter according to its significance in solving the global optimization problem.

By virtue of the systems, processes, and methods of the present disclosure, an explanation is extracted from the solution of the global optimization problem and produced as output, the output advantageously taking the form of a list or index that specifies the contemplated ranked order of significance for all model parameters of the model. The output can then be used as an explanation that is provided as input to many important use-case scenarios, including various systems, processes, or methods, all of which are predicated on the explanation, i.e., the sorted list or index of model parameters.

Illustrative use-case scenario examples abound. First, for instance, and without limitation, discovery of significant model parameters are enabled wherein the explanation is used to identify which model parameters are the most significant in solving the global optimization problem. Second, normalization of model data via insignificant model parameters is enabled wherein the explanation is used to identify which model parameters are insignificant; and, select insignificant model parameters are used to normalize model data (e.g., training data for an artificial neural network) between scientific experiments performed by different research groups or with different data collection processes and methods. Third, the validation or falsification of a scientific hypotheses is enabled wherein the explanation is used to confirm or deny that select model parameters have a high or low significance, whichever the case may be, according to the scientific hypothesis. Fourth, model adjustment or refinement is enabled wherein select model parameters of low significance are deleted from the model, thereby reducing the complexity of the model and improving the overall speed and performance of the model.

As can be readily appreciated, these examples are illustrative, and the explanation provided by the present disclosure methodology may be suitable for use in other use-case scenarios which are not expressly disclosed. It is assumed that an ordinary person skilled in the art will understand that the capability and benefits may apply, without limitation, to many use-case domains such as medical imaging in life sciences, real-time surveillance and threat detection in defense, fraud detection in finance, signal filtering in wireless communications, and augmented reality in manufacturing, just to name a few.

What has been described and depicted herein are preferred, non-limiting embodiments of Applicant's subject matter. Since the elements of the system and/or devices or mechanisms disclosed herein may be embodied in other specific forms without departing from the spirit or general characteristics thereof, some of which forms have been indicated, the embodiments described and depicted herein/with are to be considered in all respects illustrative and not restrictive. Moreover, while nominal operational steps or sequences and/or a protocol have been set forth in relation to a desirable, and advantageous processing methodology, referenced, contemplated sequences/protocols are not so limited. Accordingly, the scope of the subject invention is as defined in the language of the appended claims, and includes not insubstantial equivalents thereto.

That which is claimed:

1. A method for generating an explanation from a solution of a global optimization problem for an artificial neural network model (ANN), the method including:

determining the solution to the global optimization problem for the ANN by:

initializing each ANN parameter of a set of model parameters with an interval having a lower bound and an upper bound, the initialized model parameters defining an axis-aligned parallelotope that defines a search region;

iteratively bisecting the search region into subdomains;

for each subdomain, evaluating an objective function using modal interval arithmetic to compute an interval enclosure;

eliminating subdomains proven not to contain a global minimum based on the interval enclosure;

continuing the iterative bisecting until obtaining the solution comprising a set of solution intervals, each solution interval delimited by a first endpoint and a second endpoint;

deriving a ranked order of significance for a solution interval in the set of solution intervals as a function of the first and second endpoints of said solution interval, wherein deriving includes:

retrieving from a respective first endpoint and a respective second endpoint of each respective solution interval;

computing a distance value between the respective first endpoint and the respective second endpoint by calculating an absolute value of a difference between the respective first endpoint and the respective second endpoint; and assigning a significance metric for the respective solution interval based on the distance value;

sorting model parameters in the set of model parameters as a function of the assigned significance metrics;

generating an output comprising a list or an index that maps each ANN parameter to its ranked order of significance; and providing the output as an explanation for the solution of the global optimization problem.

2. The method of claim 1 wherein said deriving the ranked order of significance comprises obtaining a logarithmic value of a distance between said first and second endpoints of said solution interval.

3. The method of claim 1 wherein the global optimization problem is a supervised machine learning problem.

4. The method of claim 1 wherein the model parameters correspond to all of the model parameters in the set of model parameters.

5. The method of claim 1 wherein the model parameters correspond to a select set of model parameters in the set of model parameters.

6. The method of claim 5 wherein the select set of model parameters are input features of the model.

7. The method of claim 5 wherein the select set of model parameters are output features of the model.

8. The method of claim 1 wherein the explanation is provided as input to a use-case scenario, the use-case scenario predicated on the explanation.

9. The method of claim 8 wherein the use-case scenario is a discovery of significant model parameters, and the explanation is used to identify which model parameters are most significant in solving the global optimization problem.

10. The method of claim 8 wherein the use-case scenario is a normalization of model data using insignificant model parameters, and the explanation is used to identify which model parameters are insignificant, select insignificant model parameters used to normalize model data between scientific experiments performed by different research groups and/or with different data collection processes and methods.

11. The method of claim 8 wherein the use-case scenario is a validation or falsification of a scientific hypotheses, and the explanation is used to confirm or deny that select model parameters have a high or low significance in relation to the scientific hypothesis.

12. The method of claim 8 wherein the use-case scenario is a model adjustment or refinement, select model parameters of low significance deleted from the model in furtherance of reducing the complexity of the model and improving overall speed and performance of the model.

* * * * *